(12) United States Patent
Martin

(10) Patent No.: US 11,571,217 B2
(45) Date of Patent: Feb. 7, 2023

(54) METHOD AND DEVICE FOR SECLUDING A BODY VESSEL

(71) Applicant: BASIS MEDICAL, LLC, Atlanta, GA (US)

(72) Inventor: David A. Martin, Atlanta, GA (US)

(73) Assignee: BASIS MEDICAL, LLC, Atlanta, GA (US)

( * ) Notice: Subject to any disclaimer, the term of this patent is extended or adjusted under 35 U.S.C. 154(b) by 0 days.

(21) Appl. No.: 15/929,937

(22) Filed: May 29, 2020

(65) Prior Publication Data
US 2020/0289127 A1 Sep. 17, 2020

Related U.S. Application Data

(63) Continuation-in-part of application No. 14/978,021, filed on Dec. 22, 2015, now Pat. No. 11,166,729.

(51) Int. Cl.
*A61B 17/12* (2006.01)
*A61M 25/10* (2013.01)

(52) U.S. Cl.
CPC .. *A61B 17/12136* (2013.01); *A61B 17/12031* (2013.01); *A61B 17/12045* (2013.01);
(Continued)

(58) Field of Classification Search
CPC ........ A61B 17/12045; A61B 17/00008; A61B 17/12186; A61B 2017/00778; A61B 2017/1205; A61B 2090/3782; A61B 2090/378; A61B 2090/3788; A61B 2090/3786; A61B 17/12109; A61B 17/12136; A61B 17/12031; A61B 2017/12127; A61B 2217/005; A61B 2217/007; A61M 25/10; A61M 25/1011;
(Continued)

(56) References Cited

U.S. PATENT DOCUMENTS 5,022,399 A 6/1991 Biegeleisen
5,224,938 A 7/1993 Fenton, Jr.
(Continued)

OTHER PUBLICATIONS

International Search Report and Written Opinion for corresponding International Application No. PCT/US2016/033510, dated Aug. 5, 2016.
(Continued)

*Primary Examiner* — Kami A Bosworth
*Assistant Examiner* — Alexandra Lalonde
(74) *Attorney, Agent, or Firm* — Moore & Van Allen PLLC; Sydney E. McKinney; Lauren E. Burrow

(57) ABSTRACT

A device for secluding a body vessel may include a distal balloon, a proximal balloon, an aspiration port positioned adjacent to the distal balloon, an injection port positioned adjacent to the proximal balloon, and a lumen assembly. The lumen assembly may comprise a central lumen, a distal balloon lumen operably coupled to the distal balloon, a proximal balloon lumen operably coupled to the proximal balloon, an aspiration port lumen operably coupled to the aspiration port, and an injection port lumen operably coupled to the injection port. The distal balloon and the proximal balloon may define a treatment chamber therebetween, and the aspiration port and the injection port may be positioned within the treatment chamber on the lumen assembly.

17 Claims, 12 Drawing Sheets

(52) U.S. Cl.
CPC ... *A61B 17/12109* (2013.01); *A61B 2217/005* (2013.01); *A61B 2217/007* (2013.01); *A61M 25/1011* (2013.01); *A61M 2025/1052* (2013.01)

(58) Field of Classification Search
CPC .......... A61M 25/0075; A61M 25/0125; A61M 25/007; A61M 25/0032; A61M 25/0029; A61M 2025/1015; A61M 2025/1061; A61M 2025/1052; A61M 25/003; A61M 2025/0036; A61M 2025/1013; A61M 2025/0076; A61M 2025/004
See application file for complete search history.

(56) References Cited

U.S. PATENT DOCUMENTS

| | | | |
|---|---|---|---|
| 5,314,409 A * | 5/1994 | Sarosiek | A61M 25/1011 604/101.03 |
| 5,460,610 A | 10/1995 | Don Michael | |
| 5,662,609 A | 9/1997 | Slepian | |
| 8,162,879 B2 | 4/2012 | Hattangadi et al. | |
| 8,603,064 B2 | 12/2013 | Hattangadi et al. | |
| 2002/0010418 A1 * | 1/2002 | Lary | A61M 25/10 604/101.04 |
| 2004/0225251 A1 * | 11/2004 | Glickman | A61M 1/3615 604/8 |
| 2005/0273050 A1 * | 12/2005 | Yokoyama | A61M 25/1011 604/101.03 |
| 2006/0095015 A1 * | 5/2006 | Hobbs | A61B 17/12186 604/508 |
| 2009/0150782 A1 | 6/2009 | Baek et al. | |
| 2009/0203995 A1 | 8/2009 | Matonick | |
| 2009/0318855 A1 * | 12/2009 | Ehrenreich | A61M 25/1011 604/28 |
| 2010/0082012 A1 | 4/2010 | Hattangadi et al. | |
| 2011/0218494 A1 * | 9/2011 | Gerrans | A61B 17/320725 604/101.05 |
| 2012/0259215 A1 * | 10/2012 | Gerrans | A61M 25/1011 600/435 |
| 2012/0310269 A1 | 12/2012 | Fearnot | |
| 2014/0046243 A1 | 2/2014 | Ray et al. | |
| 2014/0150782 A1 | 6/2014 | Vazales et al. | |
| 2014/0163525 A1 | 6/2014 | Stamberg | |
| 2015/0174379 A1 | 6/2015 | Bagaoisan et al. | |
| 2015/0190127 A1 | 7/2015 | Madsen et al. | |
| 2015/0209560 A1 * | 7/2015 | Teeslink | A61B 17/12109 604/509 |
| 2015/0343136 A1 * | 12/2015 | Nitzan | A61M 1/34 604/6.09 |
| 2017/0232238 A1 * | 8/2017 | Biller | A61M 25/0032 604/509 |
| 2018/0193610 A1 | 7/2018 | Salerno | |
| 2019/0209176 A1 | 7/2019 | Martin | |
| 2020/0289127 A1 | 9/2020 | Martin | |

OTHER PUBLICATIONS

Ninia, Jerry G., "Treatment of Vulvar Varicosities by Injection-Compression Sclerotherapy"; Dermatologic Surgery 1997;23:573-575.

International Search Report and Written Opinion for PCT/US2021/032207 (ISA/US) dated Aug. 31, 2021.

* cited by examiner

METHOD AND DEVICE FOR SECLUDING A BODY VESSEL

CROSS-REFERENCE TO RELATED APPLICATION

This application is a continuation-in-part of, and claims the benefit of priority to, U.S. patent application Ser. No. 14/978,021, filed on Dec. 22, 2015, the content of which is incorporated herein by reference in its entirety for all purposes.

FIELD OF THE INVENTION

The following invention generally relates to the field of body vessel seclusion.

BACKGROUND OF THE INVENTION

For certain medical conditions, it may be necessary or desirable to seclude (i.e., to close off, collapse, or significantly narrow) a body vessel such as a vein or artery. One situation in which seclusion may be desirable is in the treatment of varicose veins, which are swollen, twisted, or enlarged veins that may be visible under a patient's skin. By closing off the varicose vein, blood ceases to flow in the varicose vein and is naturally redirected to healthy veins. Over time, the closed-off vein may be completely absorbed into surrounding tissue.

There are several techniques currently in use for secluding a blood vessel such as a varicose vein. Examples of these techniques include surgery, heat ablation, and chemical treatment. Surgically, veins may be subjected to a seclusion procedure known as ligation. During ligation, a small incision may be made near the target vein and the vein may be tied off. The ligated vein may be left in place and absorbed into surrounding tissue, as noted above. Alternatively, the ligated vein may be removed by a process known as "stripping" the vein. The surgical treatment of veins in this manner is sometimes referred to as phlebectomy.

The surgical treatment of varicose veins is generally effective, but may carry certain risks and disadvantages. The procedure is relatively invasive compared to other varicose vein treatment methods, and accordingly may be painful for some patients. Surgical treatment of varicose veins also carries a risk of nerve injury, may require the use of general anesthesia and an overnight hospital stay, and may require a relatively long recovery time. Accordingly, other types of vein treatment have been developed. These treatments generally involve damaging the walls of the vein, which causes the vein walls to collapse, close, or narrow. For example, in heat ablation treatment, a heat source (typically a laser or radio frequency transmitter) may be inserted into the vein through a catheter. Upon reaching a target area of the vein, the heat source may be turned on for a predetermined period of time, which damages the target area of the vein and causes scar tissue to form on the inner walls of the vein. The build-up of scar tissue closes the vein. Problematically, the same heat that damages the vein can also damage surrounding tissue and nearby nerves. It can also cause skin burns and blood clots, and may not be appropriate for all types of veins.

The vein walls can also be damaged chemically in a procedure known as sclerotherapy. In sclerotherapy, a chemical known as a sclerosing agent may be injected into the vein. The sclerosing agent may damage the walls of the vein and cause the vein to narrow or close. However, in order to be effective, the sclerosing agent needs to remain in contact with the inside walls of the target area of the vein for some time (e.g., up to one minute). This is difficult to achieve using conventional sclerotherapy procedures because the sclerosing agent may be quickly washed away by the flow of blood through the vein. As a result, the sclerosing agent may be diluted and flow to other portions of the body, and hence the sclerosing agent may not be sufficiently effective to close the vein upon an initial application. Accordingly, patients may need several treatment sessions with one or more injections of sclerosing agent applied in each session. In order to address these issues, a new sclerotherapy treatment method called catheter-directed foam sclerotherapy ("CDFS") has recently been employed. In this method, a catheter is inserted into the vein and moved to the target site. The sclerosing agent is injected into the vein through the catheter in the form of a foam. Because the agent is a foam, it is relatively more difficult for the blood flow to dilute and remove the sclerosing agent. Therefore, as compared to conventional sclerotherapy, CDFS allows the sclerosing agent to be present at the target site for a relatively longer period of time, in a relatively larger concentration. Nonetheless, the sclerosing agent will still be washed away from the target site due to the flow of the blood in the vein, so repeated treatments may remain necessary.

Therefore there at least remains a need in the art for a method and device for secluding a body vessel such that a sclerosing agent may be maintained at the target site without being washed away due to blood flow in the vessel.

SUMMARY OF THE INVENTION

One or more embodiments of the invention may address one or more of the aforementioned problems. In an example embodiment, a lumen assembly of a body vessel seclusion device is provided. The lumen assembly includes an aspiration port lumen defining a plurality of aspiration ports. The aspiration port lumen and the plurality of aspiration ports being configured to remove at least one of blood, a bodily fluid, a chemical agent for permanently secluding a body vessel, or any combination thereof from a treatment chamber in a body vessel. The lumen assembly also includes an injection port lumen defining a plurality of injection ports. The injection port lumen and the injection ports being configured to deliver the chemical agent for permanently secluding the body vessel to the treatment chamber. The lumen assembly also includes a proximal balloon lumen. The proximal balloon lumen being configured to adjust an inflation level of a proximal balloon. The lumen assembly further includes a distal balloon lumen. The distal balloon lumen being configured to adjust an inflation level of a distal balloon. The aspiration port lumen and the injection port lumen are disposed along a first transverse axis, and the proximal balloon lumen and the distal balloon lumen are disposed along a second transverse axis. The aspiration port lumen includes an aspiration port lumen diameter, the injection port lumen includes an injection port lumen diameter, the proximal balloon lumen includes a proximal balloon lumen diameter, the distal balloon lumen includes a distal balloon lumen diameter, and each of the aspiration port lumen diameter and the injection port lumen diameter are larger than each of the proximal balloon lumen diameter and the distal balloon lumen diameter.

In some embodiments, the first transverse axis is perpendicular to the second transverse axis. In some embodiments, the first transverse axis is vertical, and the second transverse axis is horizontal. In some embodiments, the plurality of aspiration ports are evenly spaced on the aspiration port lumen. In some embodiments, the aspiration port lumen includes three aspiration ports, and the injection port lumen includes four injection ports. In some embodiments, the three aspiration ports include a proximal aspiration port, an intermediate aspiration port, and a distal aspiration port, the four injection ports include a first set of two injection ports and a second set of two injection ports, the first set of two injection ports is disposed between the proximal aspiration port and the intermediate aspiration port in the treatment chamber, and the second set of two injection ports is disposed between the intermediate aspiration port and the distal aspiration port in the treatment chamber.

In some embodiments, at least one of the aspiration port lumen, the injection port lumen, the proximal balloon lumen, or the distal balloon lumen has a circular cross-section. In some embodiments, the lumen assembly has the same length as the body vessel seclusion device. In some embodiments, at least one of the aspiration port lumen and the injection port lumen is configured to receive a guide wire. In some embodiments, the proximal balloon lumen and the distal balloon lumen are configured to independently inflate the proximal balloon and distal balloon respectively.

In another example embodiment, a method of permanently secluding a body vessel is provided. The method includes adjusting an inflation level of a distal balloon via a distal balloon lumen. The method also includes adjusting an inflation level of a proximal balloon via a proximal balloon lumen. The method further includes removing blood from a treatment chamber in the body vessel via an aspiration port lumen having a plurality of aspiration ports in fluid communication with the treatment chamber. The method still further includes delivering a chemical agent to the treatment chamber via an injection port lumen having a plurality of injection ports in fluid communication with the treatment chamber. The method also includes removing the chemical agent from the treatment chamber via the aspiration port lumen. The aspiration port lumen and the injection port lumen are disposed along a first transverse axis, and the proximal balloon lumen and the distal balloon lumen are disposed along a second transverse axis. The aspiration port lumen includes an aspiration port lumen diameter, the injection port lumen includes an injection port lumen diameter, the proximal balloon lumen includes a proximal balloon lumen diameter, the distal balloon lumen includes a distal balloon lumen diameter, and each of the aspiration port lumen diameter and the injection port lumen diameter are larger than each of the proximal balloon lumen diameter and the distal balloon lumen diameter.

In some embodiments, the proximal balloon lumen and the distal balloon lumen are configured to independently inflate the proximal balloon and distal balloon respectively. In some embodiments, the first transverse axis is perpendicular to the second transverse axis. In some embodiments, the first transverse axis is vertical, and the second transverse axis is horizontal. In some embodiments, the plurality of aspiration ports are evenly spaced on the aspiration port lumen. In some embodiments, the aspiration port lumen includes three aspiration ports, and the injection port lumen includes four injection ports. In some embodiments, the three aspiration ports include a proximal aspiration port, an intermediate aspiration port, and a distal aspiration port, the four injection ports include a first set of two injection ports and a second set of two injection ports, the first set of two injection ports is disposed between the proximal aspiration port and the intermediate aspiration port in the treatment chamber, and the second set of two injection ports is disposed between the intermediate aspiration port and the distal aspiration port in the treatment chamber.

In some embodiments, at least one of the aspiration port lumen, the injection port, the proximal balloon lumen, or the distal balloon lumen has a circular cross-section. In some embodiments, the lumen assembly has the same length as the body vessel seclusion device. In some embodiments, at least one of the aspiration port lumen and the injection port lumen is configured to receive a guide wire.

In one aspect, a device for secluding a body vessel is provided. In accordance with certain embodiments, the device may include a distal balloon, a proximal balloon, an aspiration port positioned adjacent to the distal balloon, an injection port positioned adjacent to the proximal balloon, and a lumen assembly. The lumen assembly may comprise a central lumen, a distal balloon lumen operably coupled to the distal balloon, a proximal balloon lumen operably coupled to the proximal balloon, an aspiration port lumen operably coupled to the aspiration port, and an injection port lumen operably coupled to the injection port. The distal balloon and the proximal balloon may define a treatment chamber therebetween, and the aspiration port and the injection port may be positioned within the treatment chamber on the lumen assembly.

In another aspect, a method for secluding a body vessel is provided. In accordance with certain embodiments, the method may include removing blood from a treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port. The aspiration port may be operably coupled to an aspiration port lumen of a vessel seclusion device, and the injection port may be operably coupled to an injection port lumen of the vessel seclusion device.

In yet another aspect, another method for secluding a body vessel is provided. In accordance with certain embodiments, the method may include selecting a seclusion length of the body vessel such that the seclusion length has a starting point and an ending point, dividing the seclusion length into at least two treatment chambers, secluding the first treatment chamber with a vessel seclusion device, moving the vessel seclusion device to the second treatment chamber, and secluding the second treatment chamber. The first treatment chamber may be defined by the starting point and a first intermediate point, and the second treatment chamber may be defined by the first intermediate point and the ending point. Secluding each of the first treatment chamber and the second treatment chamber may comprise removing blood from the treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port. The aspiration port may be operably coupled to an aspiration port lumen of a vessel seclusion device, and the injection port may be operably coupled to an injection port lumen of the vessel seclusion device.

BRIEF DESCRIPTION OF THE DRAWINGS

Exemplary embodiments now will be described more fully hereinafter with reference to the accompanying drawings, in which some, but not all embodiments of the invention are shown. The present invention may be embodied in many different forms and should not be construed as limited to the embodiments set forth herein; rather, these embodiments are provided so that this disclosure will satisfy applicable legal requirements and demonstrate exemplary embodiments of the invention. Repeat use of reference characters in the present specification and drawings is intended to represent same or analogous features or elements of the invention.

DETAILED DESCRIPTION OF EXEMPLARY EMBODIMENTS

Figure 1:
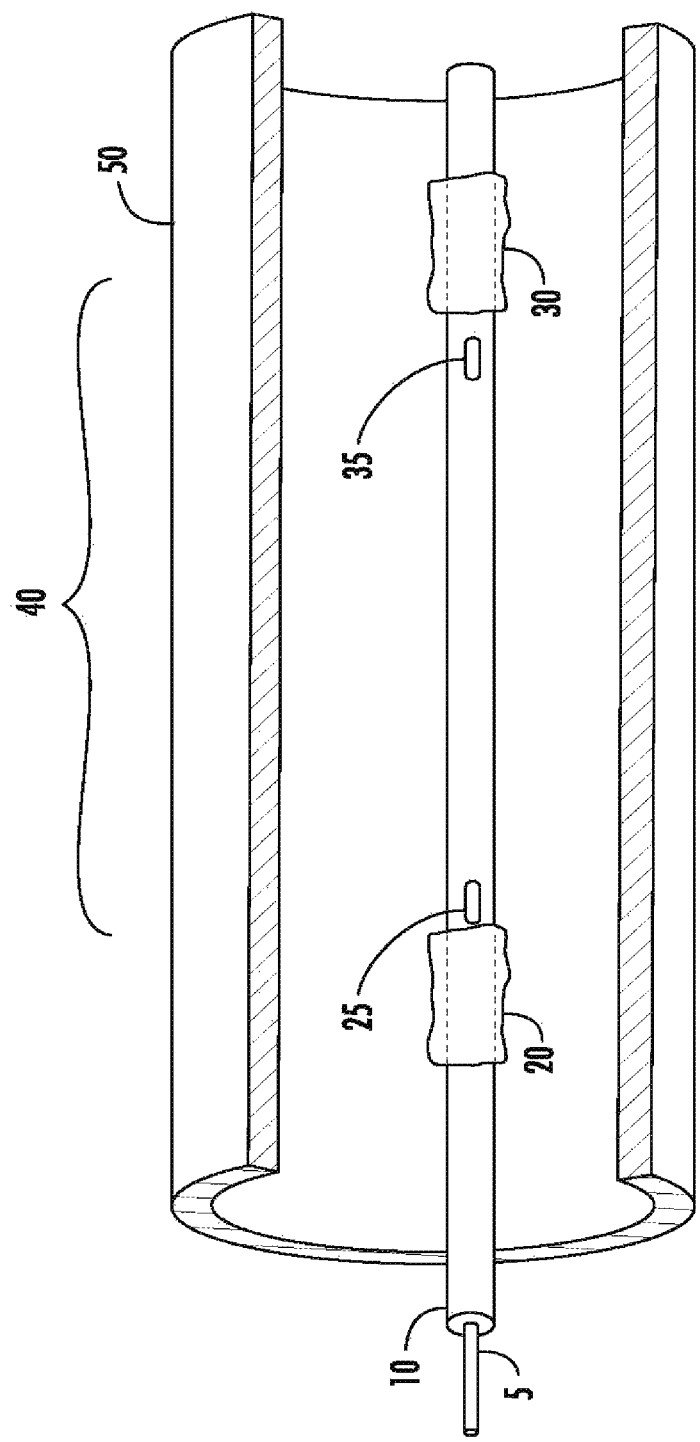
FIG. 1 illustrates a partial view of a device for secluding a body vessel in a pre-deployed form according to an example embodiment.

Reference will now be made in detail to exemplary embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

In contrast to conventional treatment methods and devices, the exemplary embodiments disclosed herein may be less invasive and may require less recovery time. Moreover, the exemplary embodiments disclosed herein may eliminate the need for a general anesthetic, instead relying on a local anesthetic. In this regard, the exemplary embodiments disclosed herein may reduce procedural risks and further decrease required recovery time. In addition, the exemplary embodiments disclosed herein may be associated with a reduced risk of nerve damage, skin damage, and recovery pain.

As used herein, the term "body vessel" may comprise any lumen or other similar region in a body, such as a blood vessel or the intestines. Although specific examples are provided herein with reference to veins, one of ordinary skill in the art will recognize that the device and methods disclosed herein are not limited to these particular examples but rather may be employed in any suitable body vessel.

The term "seclusion", as used herein, may refer to the narrowing, collapsing, or closing off of a body vessel. Accordingly, seclusion may be distinct from therapies intended to open or widen a vessel and from therapies intended to prevent the vessel from narrowing. The term "two-point seclusion", as used herein, may refer to secluding the body vessel at two points with a narrowed, collapsed, or closed space between the points.

For ease of reference, exemplary embodiments will be described in terms of use in human subjects. It will be understood, however, that such descriptions are not limited to use to humans, but will also include use in other animals unless explicitly stated otherwise. Moreover, although a catheter is referred to herein, one of ordinary skill in the art will recognize that a catheter is merely an exemplary device as disclosed herein.

In one aspect, a device for secluding a body vessel is provided. In accordance with certain embodiments, the device for secluding a body vessel may include a distal balloon, a proximal balloon, an aspiration port positioned adjacent to the distal balloon, an injection port positioned adjacent to the proximal balloon, and a lumen assembly. In some embodiments, for instance, the lumen assembly may comprise a central lumen, a distal balloon lumen operably coupled to the distal balloon, a proximal balloon lumen operably coupled to the proximal balloon, an aspiration port lumen operably coupled to the aspiration port, and an injection port lumen operably coupled to the injection port. In certain embodiments, for example, the distal balloon and the proximal balloon may define a treatment chamber therebetween, and the aspiration port and the injection port may be positioned within the treatment chamber on the lumen assembly.

FIG. 1, for instance, illustrates a partial view of a device for secluding a body vessel in a pre-deployed form according to an example embodiment. As shown in FIG. 1, for example, the device may be a catheter. The catheter may include a lumen assembly 10, a proximal balloon 20, an injection port 25 positioned adjacent to the proximal balloon 20, a distal balloon 30, and an aspiration port 35 positioned adjacent to the distal balloon 30. The proximal balloon 20 and the distal balloon 30 may define a treatment chamber 40 therebetween inside of a body vessel 50 when the balloons 20, 30 are inflated. In this regard, for example, a chemical agent may be introduced into the treatment chamber 40 to seclude the body vessel 50 within the treatment chamber 40. The balloons 20, 30 may be made of any suitable material as understood by one of ordinary skill in the art including, but not limited, to polymeric materials. In accordance with certain embodiments, for example, the body vessel 50 may comprise at least one of a varicose vein, a portal vein, a perforator vein, a superficial vein, a peripheral vein, an arteriovenous malformation, or any combination thereof. The catheter may be of any length suitable for secluding a variety of body vessels as understood by one of ordinary skill in the art (e.g., 100 cm).

According to certain embodiments, for instance, the treatment chamber 40 may comprise a length from about 3 cm to about 15 cm. In some embodiments, for example, the treatment chamber 40 may comprise a length from about 5 cm to about 10 cm. In further embodiments, for instance, the treatment chamber 40 may comprise a length from about 6 cm to about 8 cm. In certain embodiments, for example, the treatment chamber 40 may comprise a length of about 7 cm. As such, in certain embodiments, the treatment chamber 40 may comprise a length from at least about any of the following: 3, 4, 5, 6, and 7 cm and/or at most about 15, 12, 10, 9, 8, and 7 cm (e.g., about 4-9 cm, about 6-12 cm, etc.).

The lumen assembly 10 may comprise a flexible tube having several hollow lumens therein as described in more detail below. The individual lumens may not be very flexible. For example, the individual lumens within the lumen assembly 10 may only bend and/or move from about 2 mm to about 3 mm. However, the lumen assembly 10 may be sufficiently flexible to navigate through the body vessels of an individual. For instance, the lumen assembly 10 may be used to guide the device into position inside the body vessel 50, for example, via a guide wire 5.

According to certain embodiments, for instance, the guide wire 5 may comprise a diameter from about 0.001 cm to about 0.025 cm. In some embodiments, for example, the guide wire 5 may comprise a diameter from about 0.01 cm to about 0.02 cm. In further embodiments, for instance, the guide wire 5 may comprise a diameter from about 0.015 cm to about 0.019 cm. In other embodiments, for example, the guide wire 5 may comprise a diameter of about 0.018 cm. As such, in certain embodiments, the guide wire 5 may comprise a diameter from at least about any of the following: 0.001, 0.005, 0.01, 0.015, 0.016, 0.017, and 0.018 cm and/or at most about 0.025, 0.024, 0.023, 0.022, 0.021, 0.02, 0.019, and 0.018 cm (e.g., about 0.01-0.019 cm, about 0.017-0.024 cm, etc.). However, the guide wire 5 may comprise any guide wire suitable for use with the device disclosed herein as understood by one of ordinary skill in the art.

In accordance with certain embodiments, for instance, the lumen assembly 10 may include the injection port 25 and the aspiration port 35 to introduce and evacuate fluids respectively. In certain embodiments, for example, the injection port 25 and the aspiration port 35 may be positioned on the lumen assembly 10 within the treatment chamber 40 created by the inflated proximal balloon 20 and the distal balloon 30. In some embodiments, for example, each of the aspiration port 35 and the injection port 25 comprise a port orifice and a one-way valve at the port orifice. In this regard, for instance, the aspiration port 35 may evacuate blood and other bodily fluids from the treatment chamber 40 to provide an empty area for the chemical agent to occupy and to prevent the chemical agent from being diluted. Additionally, the aspiration port 35 may evacuate the chemical agent from the treatment chamber 40 after treatment. Moreover, the injection port 25 may introduce the chemical agent into the treatment chamber 40 to initiate seclusion of the body vessel 50.

Figure 2:
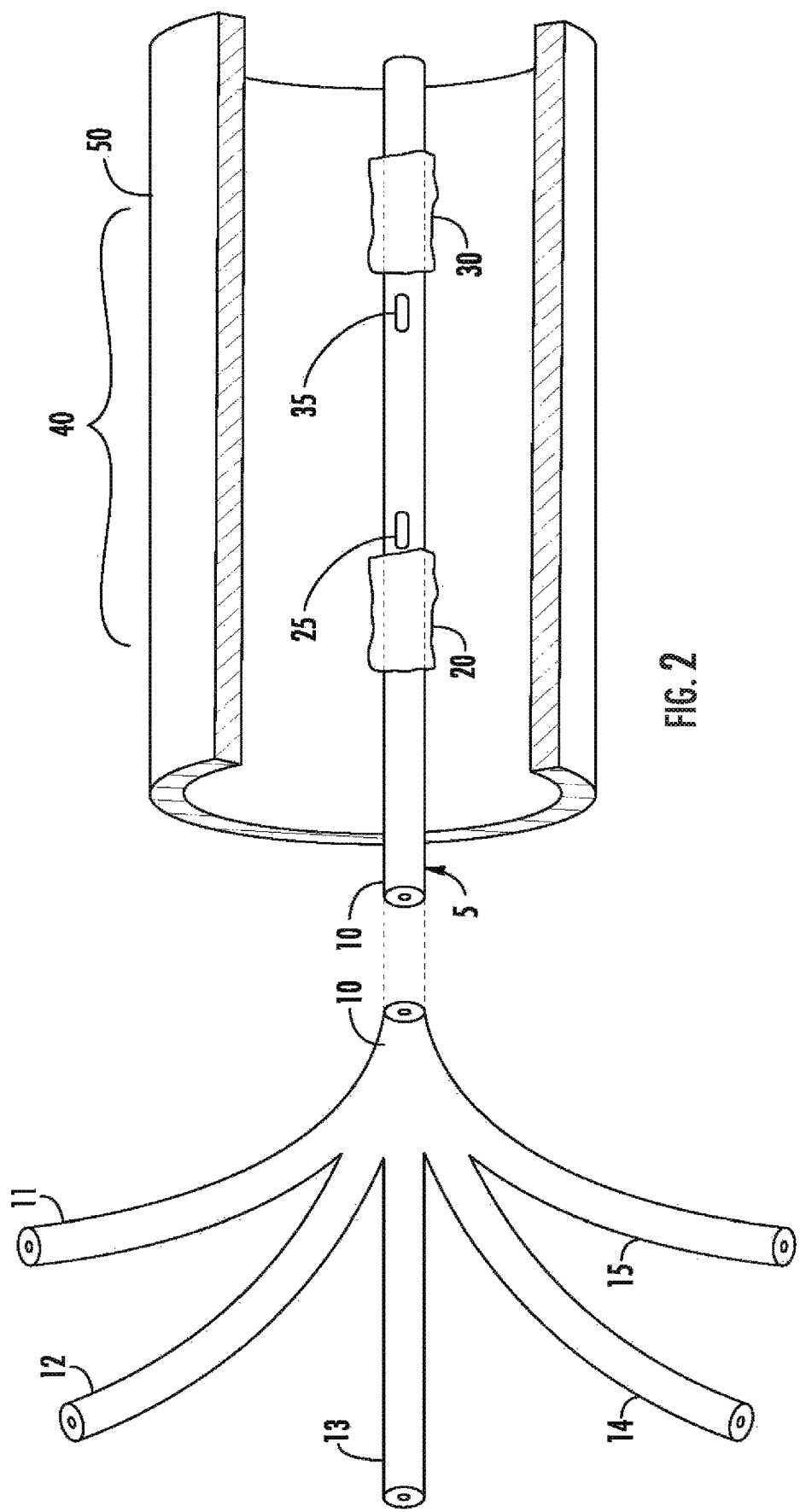
FIG. 2 illustrates a device for secluding a body vessel including the lumens according to an example embodiment.
Figure 3:
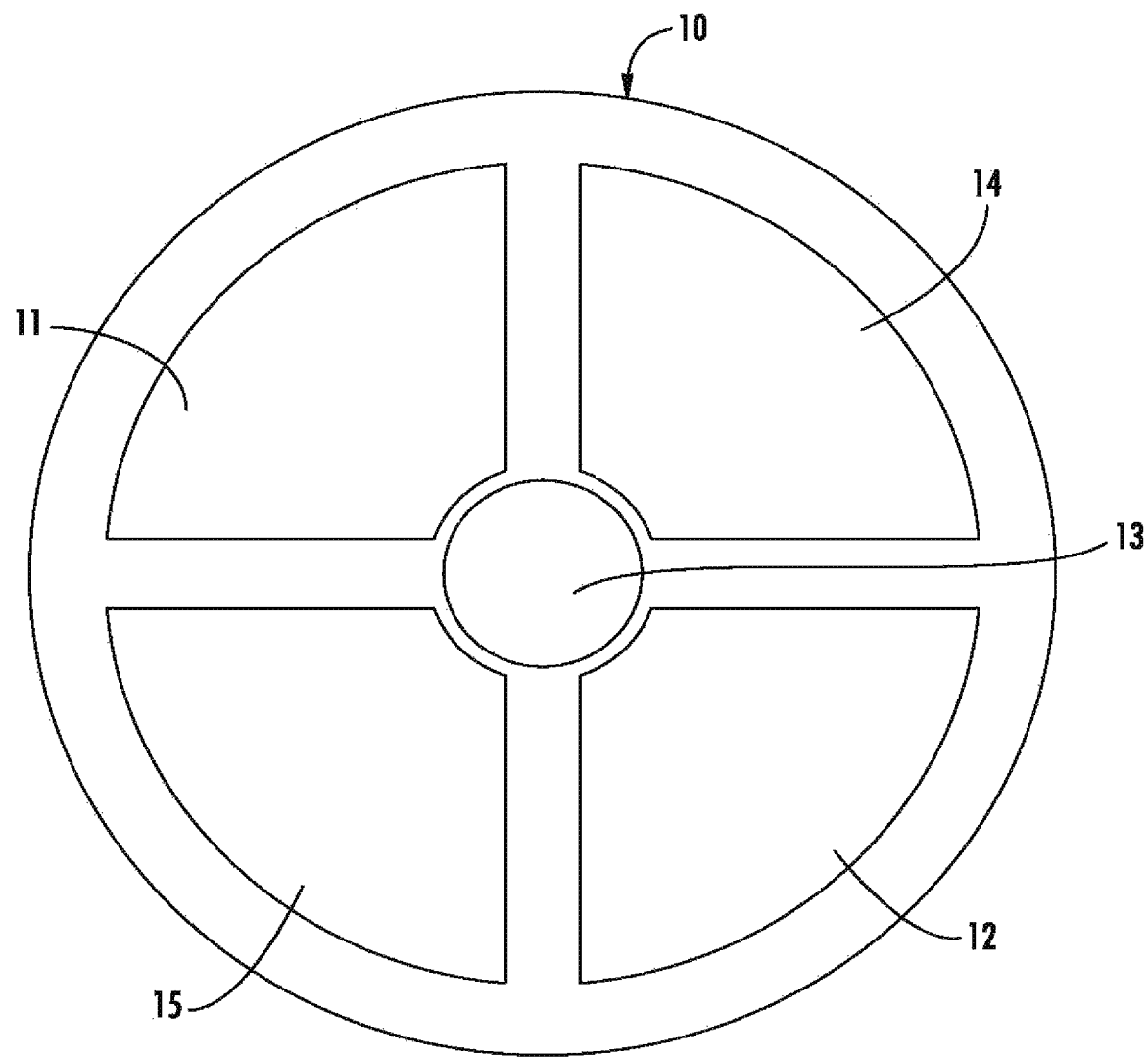
FIG. 3 illustrates a cross-section of a lumen assembly in a device for secluding a body vessel according to an example embodiment.

FIG. 2, for instance, illustrates a device for secluding a body vessel including the lumens according to an example embodiment. As shown in FIG. 2, for example, the lumen assembly 10 divides into individual lumens outside of the body vessel 50. The individual lumens include a distal balloon lumen 11, a proximal balloon lumen 12, a central lumen 13, an injection port lumen 14, and an aspiration port lumen 15. FIG. 3, for instance, illustrates a cross-section of the lumen assembly 10 in a device for secluding a body vessel according to an example embodiment. As shown in FIG. 3, for example, the lumen assembly 10 channels each of the lumens 11-15 through a single tube such that the distal balloon lumen 11, the proximal balloon lumen 12, the injection port lumen 14, and the aspiration port lumen 15 are arranged around the central lumen 13 such that the two balloon lumens 11, 12 are positioned diagonally across from each other within the lumen assembly 10. The two port lumens 14, 15 are similarly positioned diagonally across from each other within the lumen assembly 10.

According to certain embodiments, for example, the central lumen 13 is configured to introduce the guide wire 5 into the body vessel 50. Prior to the guide wire 5 moving through the central lumen 13, the body vessel 50 may be prepared. For example, an incision in a patient's skin may be made, and the body vessel 50 may be opened at the location of the incision. The guide wire 5 may then be inserted into the opening in the body vessel 50 and threaded through the body vessel 50 under guidance of a visualization device (e.g., ultrasound 95), as described in more detail below. In various embodiments, the visualization device (e.g., an ultrasound transducer 95) may be used during the operation of the catheter. For example, the ultrasound transducer may be used to position the catheter within a body vessel. In various embodiments, one or more substances used in the catheter may be visible via ultrasound, such that the movement and operation of the body vessel seclusion system may be monitored in real time during operation. For example, the ultrasound transducer may be used to monitor the contraction and/or deflection of the body vessel in an instance in which the balloons are inflated and the treatment chamber is defined (e.g., a vein may deflect approximately 1 mm in an instance in which the vein is prepared for seclusion). When the guide wire 5 reaches the appropriate treatment point within the body vessel 50, the central lumen 13 may be threaded over the guide wire 5 and into the body vessel 50. The central lumen 13 (and similarly the entire device) may be pushed along the length of the guide wire 5 until the distal balloon 30 is in a suitable location in the body vessel 50 as indicated by the visualization device.

In various embodiments, the visualization device (e.g., an ultrasound transducer 95) may be used to monitor the operation of the body vessel seclusion system in approximately real-time. In various embodiments, the visualization device (e.g., the ultrasound transducer) may monitor the balloon inflation during operation (e.g., the balloons may be filled with a substance visible under an ultrasound, such as air). In various embodiments, the visualization device (e.g., the ultrasound transducer) may be used to position the catheter within the body vessel (e.g., originally for the first treatment chamber and/or during repositioning for subsequent treatment chambers). For example, the catheter may include a reflective substance such that at least a portion of the catheter may be visible via an ultrasound. In various embodiments, the visualization device may be used to monitor the infusion and/or aspiration of the chemical agent into the body vessel during operation. For example, the chemical agent may be visible by the visualization device, such that the amount and/or distribution of chemical agent in the body vessel can be monitored (e.g., a doctor may, in some examples, be able to determine when a sufficient amount of chemical agent has been provided to the body vessel for seclusion).

According to certain embodiments, for instance, the aspiration port 35 and the aspiration port lumen 15 may be configured to remove at least one of blood, bodily fluid, a chemical agent, or any combination thereof from the treatment chamber 40. In further embodiments, for example, the injection port 25 and the injection port lumen 14 may be configured to deliver a chemical agent to the treatment chamber 40.

Moreover, according to certain embodiments, for instance, the proximal balloon 20 and the distal balloon 30 may be inflated through the proximal balloon lumen 12 and the distal balloon lumen 11 respectively. The balloons 20, 30 may be inflated using air or any other suitable fluid as understood by one of ordinary skill in the art. In this regard, the inflation of the balloons 20, 30 may secure the catheter in place and isolate the treatment chamber 40.

Figure 4:
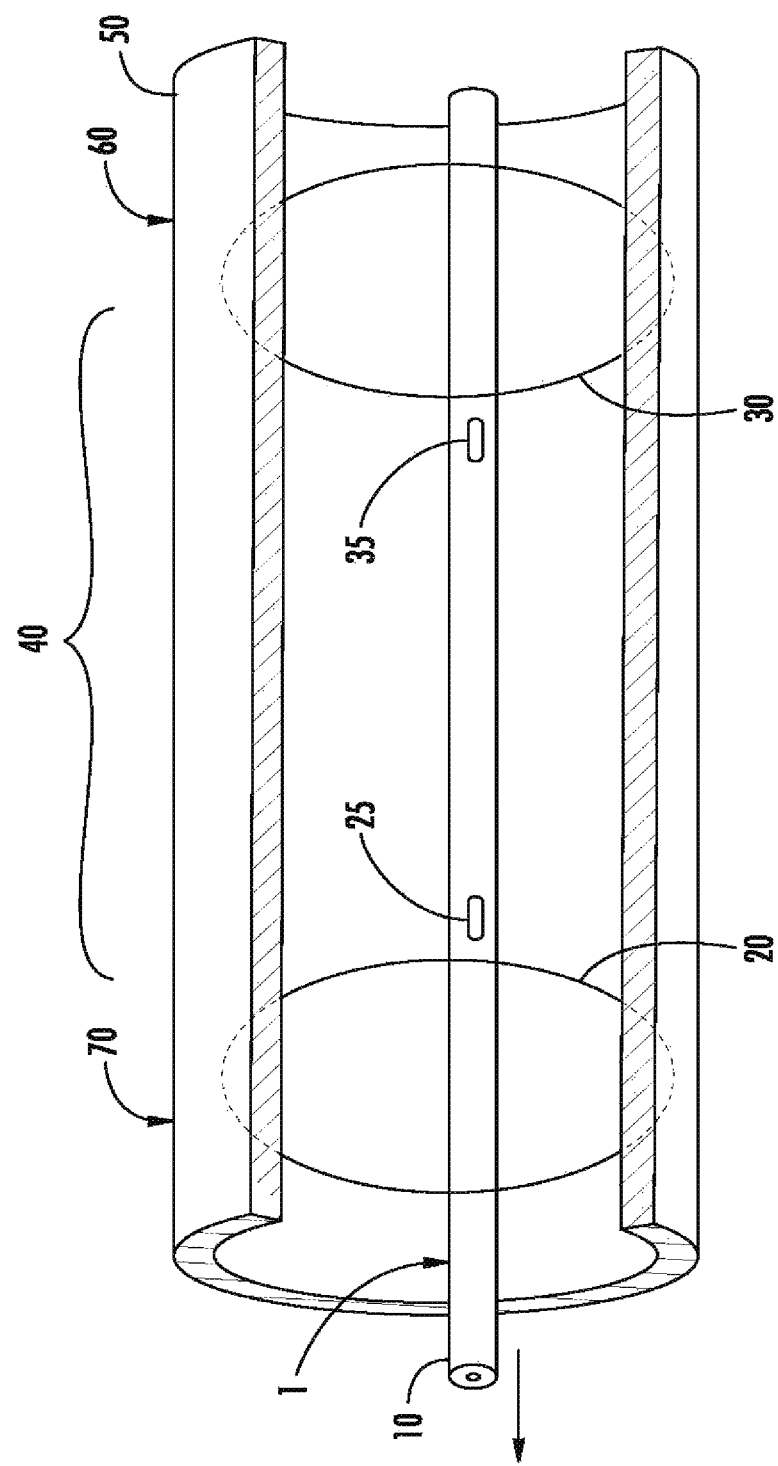
FIG. 4 illustrates a partial view of a device for secluding a body vessel in a deployed form according to an example embodiment.

FIG. 4, for example, illustrates a partial view of a device for secluding a body vessel in a deployed form according to an example embodiment. As shown in FIG. 4, for instance, the balloons 20, 30 are inflated to define the treatment chamber 40. To define the treatment chamber 40, for example, the proximal balloon 20 and the distal balloon 30 may be inflated with a fluid. When inflated, for instance, the interior sides of the distal balloon 30 and the proximal balloon 20 (i.e. the sides facing internally towards each other) may define the outer limits (e.g., starting point 60 and ending point 70) of the treatment chamber 40. For example, the proximal and distal balloons 20, 30 may be sized so that, when inflated, the outer ends of the balloons 20, 30 contact the interior surface of the body vessel 50 and form a seal, preventing fluids from entering or leaving the treatment chamber 40. According to certain embodiments, each of the distal balloon 30 and the proximal balloon 20 are spherical. However, the balloons 20, 30 may be any shape suitable for use in the device as understood by one of ordinary skill in the art.

In some embodiments, for instance, the distal balloon 30 may comprise an inflated distal balloon diameter, the proximal balloon 20 may comprise an inflated proximal balloon diameter, and each of the inflated distal balloon diameter and the inflated proximal balloon diameter may be from about 5 mm to about 20 mm. In further embodiments, for example, each of the inflated distal balloon diameter and the inflated proximal balloon diameter may be from about 7 mm to about 15 mm. In other embodiments, for instance, each of the inflated distal balloon diameter and the inflated proximal balloon diameter may be from about 8 mm to about 12 mm. As such, in certain embodiments, each of the inflated distal balloon diameter and the inflated proximal balloon diameter may be from at least about any of the following: 5, 6, 7, and 8 mm and/or at most about 20, 19, 18, 17, 16, 15, 14, 13, and 12 mm (e.g., about 6-18 mm, about 5-14 mm, etc.).

In another aspect, a method for secluding a body vessel is provided. In accordance with certain embodiments, the method may include removing blood from a treatment chamber 40 in the body vessel 50 via an aspiration port 35, delivering a chemical agent to the treatment chamber 40 via an injection port 25, maintaining the chemical agent in the treatment chamber 40 for a predetermined period of time to seclude the body vessel 50 within the treatment chamber 40, and removing the chemical agent from the treatment chamber 40 via the aspiration port 35. The aspiration port 35 may be operably coupled to an aspiration port lumen 15 of a vessel seclusion device (e.g., catheter), and the injection port 25 may be operably coupled to an injection port lumen 14 of the vessel seclusion device.

Figure 6:
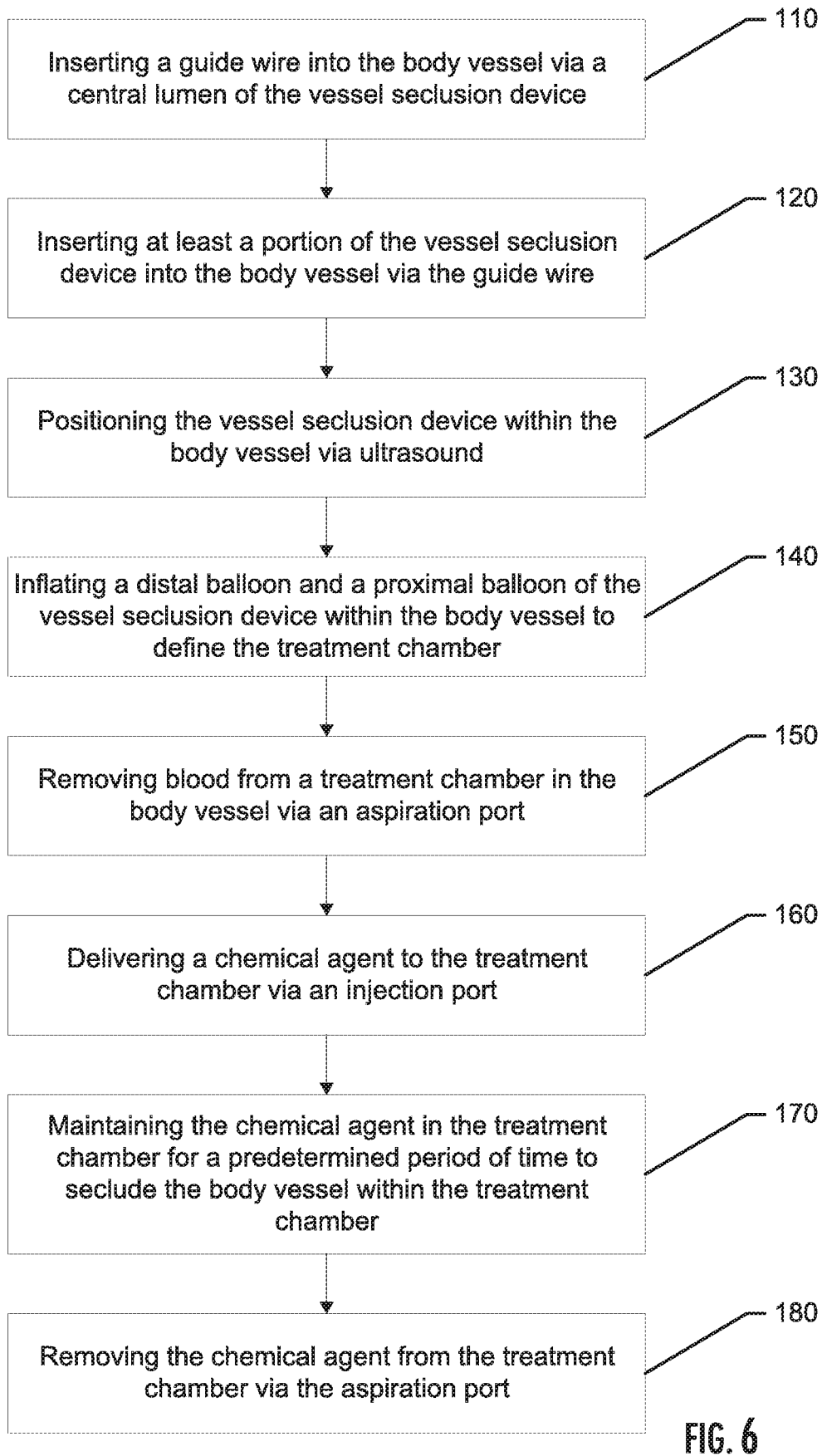
FIG. 6 illustrates a block diagram of a method of secluding a body vessel according to an example embodiment.

FIG. 6, for example, illustrates a block diagram of a method of secluding a body vessel 50 according to an example embodiment. As shown in FIG. 6, for instance, the method includes the initial steps of inserting a guide wire 5 into the body vessel 50 via a central lumen 13 of the vessel seclusion device at operation 110, inserting at least a portion of the vessel seclusion device into the body vessel 50 via the guide wire 5 at operation 120, positioning the vessel seclusion device within the body vessel 50 via ultrasound 95 at operation 130, and inflating a distal balloon 30 and a proximal balloon 20 of the vessel seclusion device within the body vessel 50 to define the treatment chamber 40 at operation 140. The method continues with the primary treatment steps of removing blood from the treatment chamber 40 in the body vessel 50 via an aspiration port 35 at operation 150, delivering a chemical agent to the treatment chamber 40 via an injection port 25 at operation 160, maintaining the chemical agent in the treatment chamber 40 for a predetermined period of time to seclude the body vessel 50 within the treatment chamber 40 at operation 170, and removing the chemical agent from the treatment chamber 40 via the aspiration port 35 at operation 180.

In accordance with certain embodiments, for instance, the chemical agent may be any agent known to chemically damage the body vessel 50 into which the catheter has been introduced, thereby causing the body vessel 50 to narrow or close. In some embodiments, for example, the chemical agent may be a sclerosing agent typically used in sclerotherapy including, but not limited to, polidocanol, sotradecol, hypertonic saline, or any other chemical agent suitable for damaging the vessel in the context of the sclerosing effect as understood by one of ordinary skill in the art. Alternatively or in addition, for instance, the chemical agent may be an agent known to elicit a biological response from the body vessel 50 into which the catheter has been introduced. In such embodiments, for example, the agent may be selected so as to induce the biological reaction substantially immediately after the catheter is withdrawn from the treatment chamber 40 (i.e. the body vessel 50 closes or narrows around the catheter as the catheter is withdrawn from the body vessel 50). In this regard, the body vessel 50 may be caused to immediately close following application of the chemical agent (as compared to traditional sclerotherapies, in which the vessel may take several days, or even several weeks, to close following application of the sclerosing agent).

According to certain embodiments, for example, after evacuating the treatment chamber 40 of all blood and/or other bodily fluids via the aspiration port lumen 15 and the aspiration port 35, a chemical agent may be introduced into the treatment chamber 40 via the injection port lumen 14 and injection port 25 and then maintained in the treatment chamber 40 for a predetermined amount of time due to the inflated balloons 20, 30. In some embodiments, for instance, maintaining the chemical agent in the treatment chamber for the predetermined period of time may comprise maintaining the chemical agent in the treatment chamber for up to one minute (i.e. from about 1 second to about 60 seconds). As such, in certain embodiments, for instance, the chemical agent may be maintained in the treatment chamber for a time from at least about any of the following: 1, 5, 10, 20, 30, 40, 50, and 60 seconds and/or at most 60 seconds (e.g., about 5-60 seconds, about 30-60 seconds, etc.). In this regard, the chemical agent remains in contact with walls of the body vessel 50 in the treatment chamber 40 for a sufficient amount of time to seclude the body vessel 50 without being diluted or washed away by the flow of fluid in the body vessel 50 shortly after introduction of the chemical agent. After the predetermined period of time, the chemical agent may be removed from the body vessel 50 via the aspiration port 35 and the aspiration port lumen 15. If the treatment chamber 40 fully encompassed the area to be secluded, the balloons 20, 30 may be deflated and the catheter may be withdrawn from the body vessel 50 through the original incision. The original incision in the body vessel 50 and/or skin may then be closed (e.g., via sutures). In this regard, the body vessel 50 may be secluded between two points (e.g., the starting point 60 and the ending point 70 in FIG. 4).

Following treatment, a patient will typically be capable of walking immediately and can return home after the procedure (i.e. the patient does not need to remain in a hospital overnight). The body vessel 50 may be secluded immediately, as opposed to conventional sclerotherapy, which may require additional time following treatment and/or multiple treatments in order to seclude the body vessel 50, and the body vessel 50 may be absorbed into surrounding tissue over a period of several months. The patient may be scheduled for a follow-up visit to verify that the body vessel 50 has been properly secluded and absorbed. If a problem is noted at the follow-up visit, for instance, the patient may undergo another round of treatment using the methods and devices disclosed herein or may be treated using a different method. In this regard, the methods disclosed herein may be used in combination with other conventional treatments.

In yet another aspect, another method for secluding a body vessel is provided. In accordance with certain embodiments, the method may include selecting a seclusion length of the body vessel such that the seclusion length has a starting point and an ending point, dividing the seclusion length into at least two treatment chambers, secluding the first treatment chamber with a vessel seclusion device (e.g., catheter), moving the vessel seclusion device to the second treatment chamber, and secluding the second treatment chamber. The first treatment chamber may be defined by the starting point and a first intermediate point, and the second treatment chamber may be defined by the first intermediate point and the ending point. Secluding each of the first treatment chamber and the second treatment chamber may comprise removing blood from the treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port as previously discussed herein. The aspiration port may be operably coupled to an aspiration port lumen of a vessel seclusion device, and the injection port may be operably coupled to an injection port lumen of the vessel seclusion device.

Figure 8:
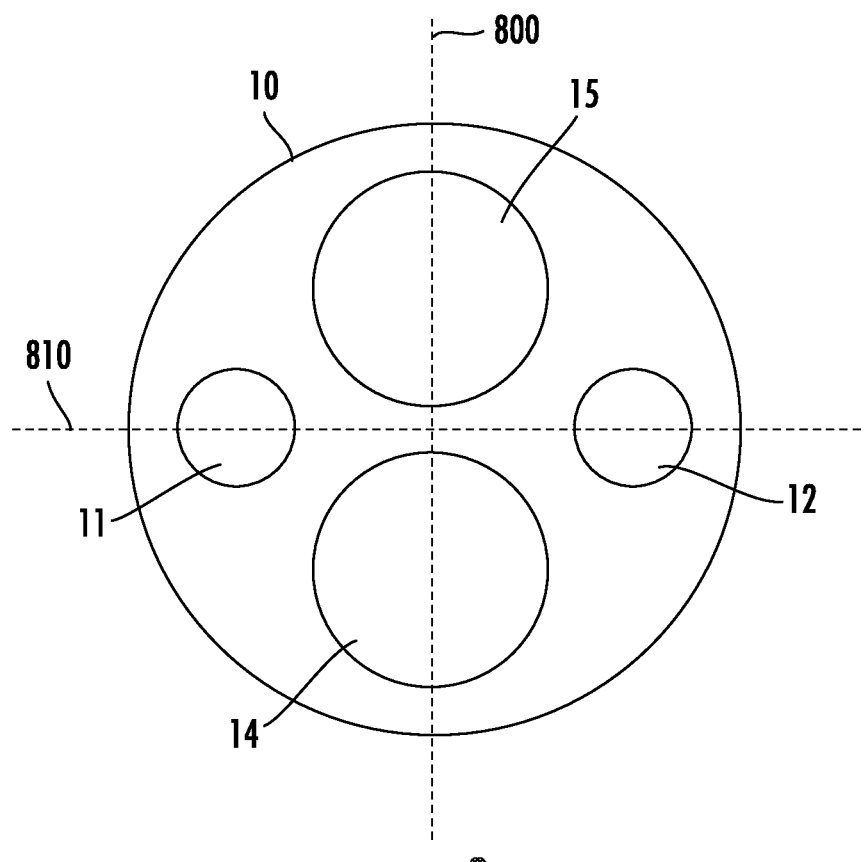
FIG. 8 illustrates a cross-section of another lumen assembly in a device for secluding a body vessel according to an example embodiment.

Lumen Assembly Without Guide Wire Lumen (FIG. 8)

In some embodiments, the number of lumens in the lumen assembly 10 may be different than shown in FIG. 2. In some embodiments, the lumen assembly 10 may be configured to function without the need for a central lumen that includes a guide wire. In some embodiments, the lumen assembly 10 may include a distal balloon lumen 11, a proximal balloon lumen 12, an injection port lumen 14, and an aspiration port lumen 15. FIG. 8, for instance, illustrates a cross-section of the lumen assembly 10 in a device for secluding a body vessel according to an example embodiment. As shown in FIG. 8, for example, the lumen assembly 10, including the distal balloon lumen 11, the proximal balloon lumen 12, the injection port lumen 14, and the aspiration port lumen 15 may be arranged in a single tube. In various embodiments, the lumen assembly 10 may be made out of a single material. In various embodiments, the lumen assembly 10 may be extruded (e.g., an extruded plastic). In various embodiments, each of the distal balloon lumen 11, the proximal balloon lumen 12, the injection port lumen 14, and the aspiration port lumen 15 may be a bore hole through the extruded material (e.g., a bore hole through the extruded plastic). The lumen assembly 10, in some examples, may have increased structural integrity due to the position of the lumen boreholes within the lumen assembly 10. For example, the material through which the bore holes are extruded may be arranged to give the lumen rigidity (i.e., the arrangement of the bore holes with respect to the material may provide additional lumen rigidity). In various embodiments, the larger diameter of the injection port lumen 14 and the aspiration port lumen 15 may be approximately perpendicular to provide lumen rigidity.

As shown in FIG. 8, in some embodiments, the aspiration port lumen 15 and the injection port lumen 14 may be generally disposed along a first transverse axis 800. In some embodiments, the proximal balloon lumen 12 and the distal balloon lumen 11 may be generally disposed along a second transverse axis 810. In some embodiments, the first transverse axis 800 and the second transverse axis 810 may be approximately perpendicular to one another. For example, in an instance the first transverse axis 800 is generally vertical, the second transverse axis 810 may be generally horizontal. In various embodiments, the first transverse axis 800 and the second transverse axis 810 may be defined along the cross-section of the lumen assembly 10 (e.g., as shown in FIG. 8). In various embodiments, the lumen assembly 10 may have a sufficient rigidity, such that, in some examples, the lumen assembly 10 is resistant to kinking, for example, during insertion into and positioning within the body lumen.

In some embodiments, at least one of the aspiration port lumen 15, the injection port lumen 14, the proximal balloon lumen 12, or the distal balloon lumen 11 may have a circular, or generally circular (e.g., an oval), cross-section. In some embodiments, the aspiration port lumen 15 may have an aspiration port lumen diameter, the injection port lumen 14 may have an injection port lumen diameter, the proximal balloon lumen 12 may have a proximal balloon lumen diameter, and the distal balloon lumen 11 may have a distal balloon lumen diameter. As shown in FIG. 8, in some embodiments, each of the aspiration port lumen diameter and the injection port lumen diameter may be larger than each of the proximal balloon lumen diameter and the distal balloon lumen diameter. In some embodiments, at least one of the aspiration port lumen 15 or the injection port lumen 14 may be configured to receive a guide wire. For example, the guide wire may be received by one or both of the aspiration port lumen 15 or the injection port lumen 14 and does not require a separate guide wire lumen.

Figure 9:
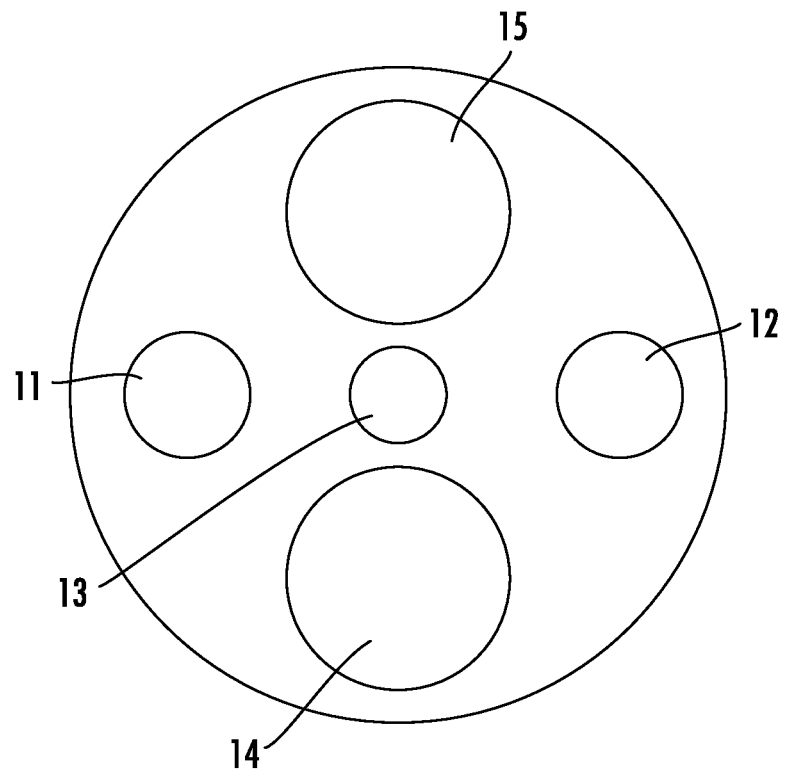
FIG. 9 illustrates a cross-section of yet another lumen assembly in a device for secluding a body vessel according to an example embodiment.

Additional Example Lumen Assembly Configuration (FIG. 9)

FIG. 9 illustrates another example lumen assembly 10 configuration including a distal balloon lumen 11, a proximal balloon lumen 12, a guide wire lumen 13, an injection port lumen 14, and an aspiration port lumen 15. As shown in FIG. 9, for example, the lumen assembly 10, including the distal balloon lumen 11, the proximal balloon lumen 12, the guide wire lumen 13, the injection port lumen 14, and the aspiration port lumen 15 may be arranged in a single tube. In some embodiments, the aspiration port lumen 15 and the injection port lumen 14 may be generally disposed along a first transverse axis 800. In some embodiments, the proximal balloon lumen 12 and the distal balloon lumen 11 may be generally disposed along a second transverse axis 810. In some embodiments, the first transverse axis 800 and the second transverse axis 810 may be approximately perpendicular to one another. For example, in a configuration in which the first transverse axis 800 is generally vertical, the second transverse axis 810 may be horizontal. In some embodiments, the guide wire lumen 13 may be located generally in the middle of the lumen assembly 10. For example, the guide wire lumen 13 may be located at approximately the intersection of the first transverse axis 800 and the second transverse axis 810.

In some embodiments, at least one of the aspiration port lumen 15, the injection port lumen 14, the proximal balloon lumen 12, the distal balloon lumen 11, or the guide wire lumen 13 may have a circular cross-section. In some embodiments, the aspiration port lumen 15 may have an aspiration port lumen diameter, the injection port lumen 14 may have an injection port lumen diameter, the proximal balloon lumen 12 may have a proximal balloon lumen diameter, the distal balloon lumen 11 may have a distal balloon lumen diameter and/or the guide wire lumen 13 may have a guide wire lumen diameter. As shown in FIG. 9, in some embodiments, each of the aspiration port lumen diameter and the injection port lumen diameter may be larger than each of the proximal balloon lumen diameter, the distal balloon lumen diameter, and the guide wire lumen diameter. In some embodiments, the guide wire lumen diameter may be smaller than the proximal balloon lumen diameter or the distal balloon lumen diameter. In various embodiments, the size of the aspiration port lumen diameter and the injection port lumen diameter may provide more rigidity to the lumen assembly 10, such that the guide wire lumen 13 does not have to be as large in order to provide similar rigidity compared to a lumen assembly with similar sized lumens, such as the lumen assembly shown in FIG. 2.

Figure 7:
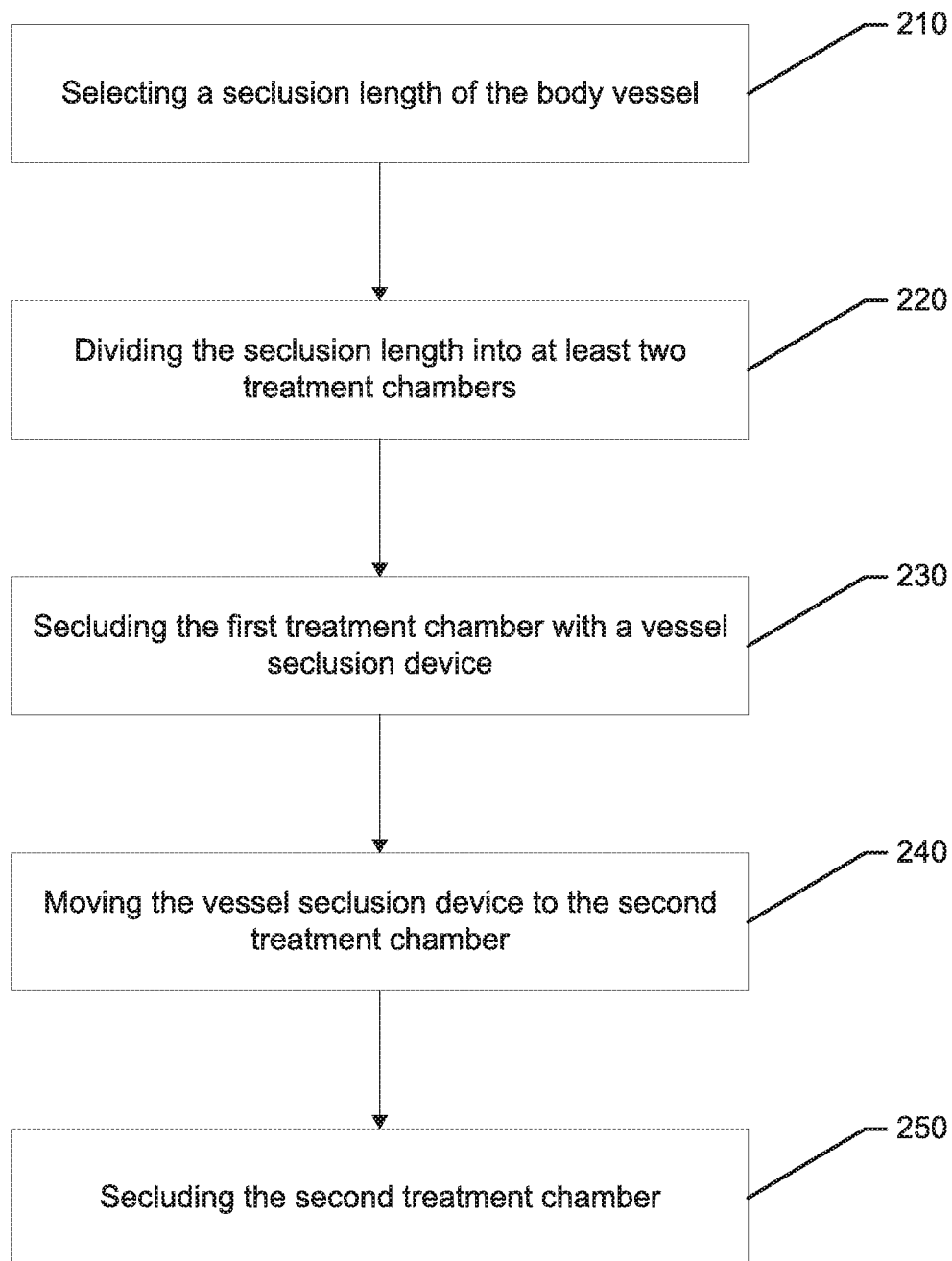
FIG. 7 illustrates a block diagram of a method of secluding a body vessel according to an example embodiment.

FIG. 7, for example, illustrates a block diagram of a method of secluding a body vessel according to an example embodiment. As shown in FIG. 7, for instance, the method includes selecting a seclusion length of the body vessel at operation 210, dividing the seclusion length into at least two treatment chambers at operation 220, secluding the first treatment chamber with a vessel seclusion device at operation 230, moving the vessel seclusion device to the second treatment chamber at operation 240, and secluding the second treatment chamber at operation 250. In this regard, if the seclusion length 100 extends beyond one treatment chamber 40, the catheter may be partially withdrawn in order to reposition the treatment chamber 40 at a new location along the seclusion length 100.

According to certain embodiments, for instance, the seclusion length 100 may be from about 3 cm to about 100 cm. In other embodiments, for example, the seclusion length 100 may be from about 7 cm to about 90 cm. In further embodiments, for instance, the seclusion length 100 may be from about 15 cm to about 80 cm. In some embodiments, for example, the seclusion length 100 may be from about 60 cm to about 70 cm. As such, in certain embodiments, the seclusion length 100 may be from at least about any of the following: 3, 5, 7, 10, 15, 20, 30, 40, 50, and 60 cm and/or at most about 100, 95, 90, 85, 80, 75, and 70 cm (e.g., about 5-70 cm, about 50-60 cm, etc.).

Figure 5:
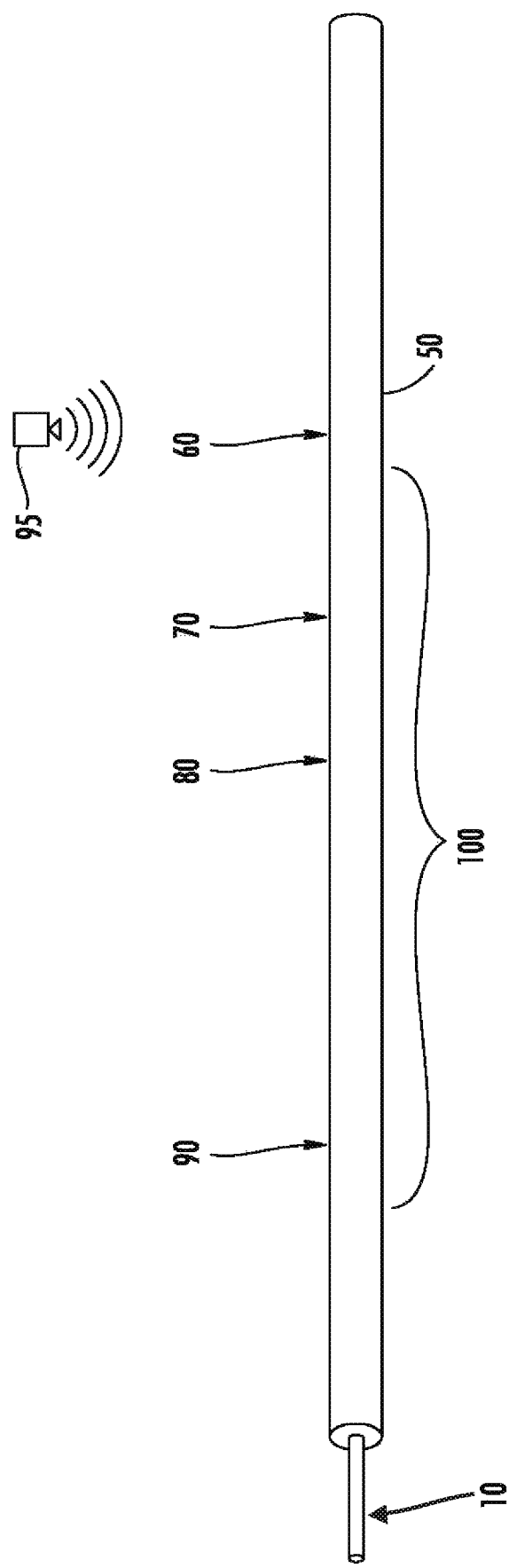
FIG. 5 illustrates a body vessel with an identified area to be secluded according to an example embodiment.

In accordance with certain embodiments, for example, the seclusion length may comprise at least three treatment chambers. In such embodiments, for instance, the first treatment chamber may be defined by the starting point and the first intermediate point, the second treatment chamber may be defined by the first intermediate point and a second intermediate point, and a third treatment chamber may be defined by the second intermediate point and the ending point. FIG. 5, for instance, illustrates a body vessel with an identified area to be secluded according to an example embodiment. As shown in FIG. 5, for example, the seclusion length 100 is divided into three treatment chambers, with the first treatment chamber to be located between the starting point 60 and the first intermediate point 70, the second treatment chamber to be located between the first intermediate point 70 and the second intermediate point 80, and the third treatment chamber to be located between the second intermediate point 80 and the ending point 90.

According to certain embodiments, moving the vessel seclusion device comprises positioning the vessel seclusion device within the body vessel 50 via ultrasound 95. Ultrasound 95 may be used to position the vessel seclusion device because it is not invasive and does not require special equipment to be deployed on the catheter or guide wire 5.

In this regard, the catheter may initially be positioned such that the treatment chamber 40 lies between the starting point 60 and the first intermediate point 70. Following application of the chemical agent between these points 60, 70, the catheter may be repositioned so that the distal balloon 30 is positioned at the first intermediate point 70 and the proximal balloon 20 is positioned at the second intermediate point 80. The method may be repeated until the full seclusion length 100 has been treated such that the proximal balloon 20 is positioned at the ending point 90.

Marking System

Figure 10A:
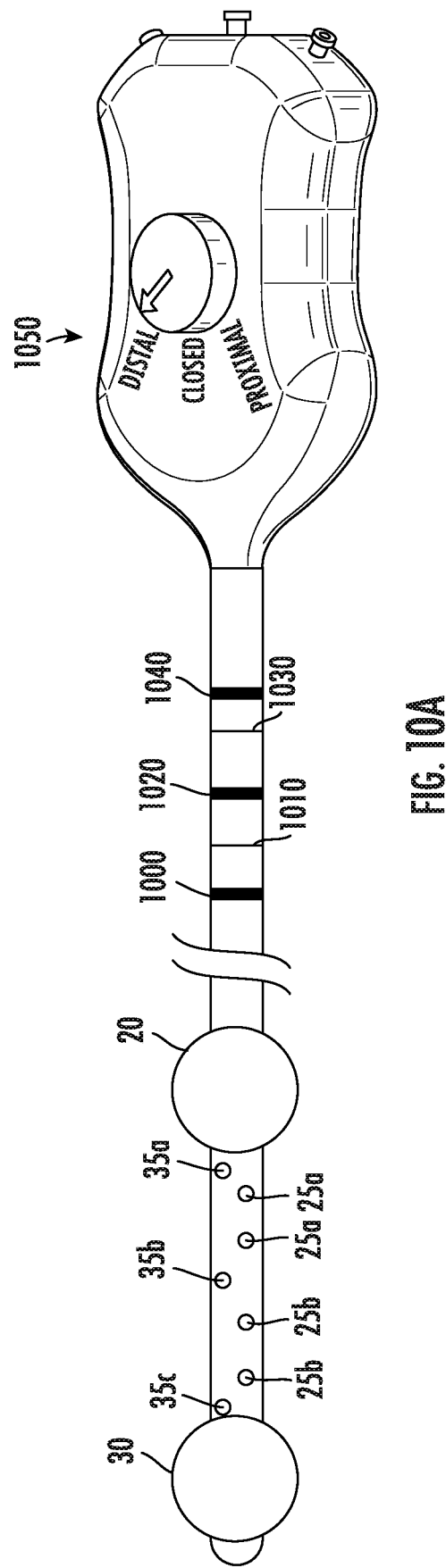
FIG. 10A illustrates a device for secluding a body vessel including the lumens and a marking system according to an example embodiment.

As shown in FIG. 10A, the lumen assembly 10 may have a plurality of markers 1000-1040 at least partially along the seclusion length 100, discussed above. In some embodiments, the plurality of markers 1000-1040 may be visible using an ultrasound. In some embodiments, the plurality of markers may be evenly spaced along the lumen assembly 10. In various embodiments, the spacing between given markers may be based on the distance between the distal balloon 30 and the proximal balloon 20. In some embodiments, the spacing between a starting point (e.g., a first marker) and an intermediate point (e.g., a second marker) may be less than the distance between the distal balloon 30 and the proximal balloon 20. For example, the distance between each marker may be approximately half of the distance between the distal balloon 30 and the proximal balloon 20. In some embodiments, the distance between adjacent markers may be approximately 1 centimeter to 10 centimeters. In some embodiments, the distance between adjacent markers may be approximately 2 centimeters to 8 centimeters. In some embodiments, the distance between adjacent markers may be approximately 7 centimeters to 7.5 centimeters. In some embodiments, the distance between adjacent markers may be approximately 7 centimeters. In some embodiments, each marker may be approximately 3 centimeters to 3.5 centimeters from the adjacent marker. In some embodiments, each marker may be approximately 3 centimeters from the adjacent marker. In various embodiments, the distance between adjacent markers may be dependent on the length of the treatment chamber (e.g., the distance between markers may be greater for a catheter with a longer treatment chamber).

Figure 10B:
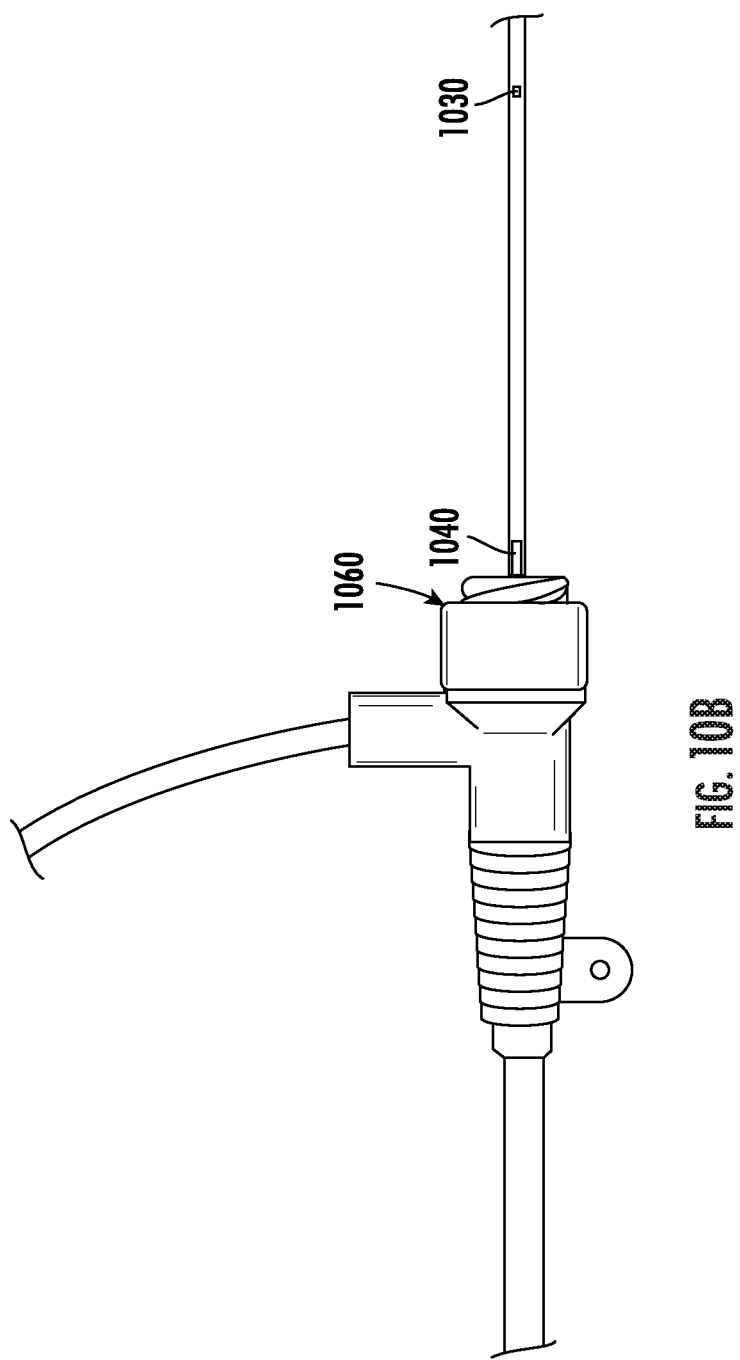
FIG. 10B illustrates the marking system and a reference point, such as an introducer, used according to an example embodiment.

In various embodiments, the position of the catheter may be based with reference to the position of the markers relative to a reference point. For example, as shown in FIG. 10B, the markers may be monitored (e.g., by ultrasound) at the location of the introducer 1060, discussed herein. In some embodiments, the reference point (e.g., the introducer 1060) may be positioned such that one of the markers aligns with the reference point in an instance in which the catheter is in the first treatment chamber location. As shown in FIG. 10B, in an instance in which the lumen assembly 10 is positioned at the first treatment chamber, one of the markers of the lumen assembly (e.g., marker 1040) may align with the end of the introducer 1060 disposed within the body vessel. For example, the introducer 1060 may be placed into the body vessel, in some examples, to stretch the body vessel and the lumen assembly may be placed into the body vessel through the introducer 1060. In various embodiments, the introducer 1060 may be placed at a known position in the body vessel (e.g., via ultrasound), such that in an instance in which the lumen assembly is placed at the first treatment chamber, one of the markers aligns with the end of the introducer (e.g., as shown in FIG. 10B).

In various embodiments, as shown in FIG. 10A, the markers may have different thicknesses based on the location along the lumen assembly. For example, in an instance in which the distance between markers is approximately half of the distance between the distal balloon 30 and the proximal balloon 20, every other marker may be wider (e.g., markers 1000, 1020, 1040), such that the user may easily move the catheter from one treatment chamber to another. For example, in an instance in which the first treatment chamber is positioned such that a bold marker (e.g., marker 1040) is located at the reference point, in order to move to a second treatment chamber, the catheter may be moved to a position at which the next bold marker (e.g., marker 1020) is located at the reference point. Alternatively, in an instance in which the first treatment chamber is positioned such that a thinner marker (e.g., marker 1030) is located at the reference point, in order to move to a second treatment chamber, the catheter may be moved to a position at which the next thinner marker (e.g., marker 1010) is located at the reference point.

In various embodiments, the plurality of markers 1000-1040 may be used to determine the placement of the lumen assembly within a body vessel during operation. In various embodiments, the method of permanently secluding a body vessel may include treating a plurality of treatment chambers along the body vessel, as discussed in FIG. 11.

Figure 11:
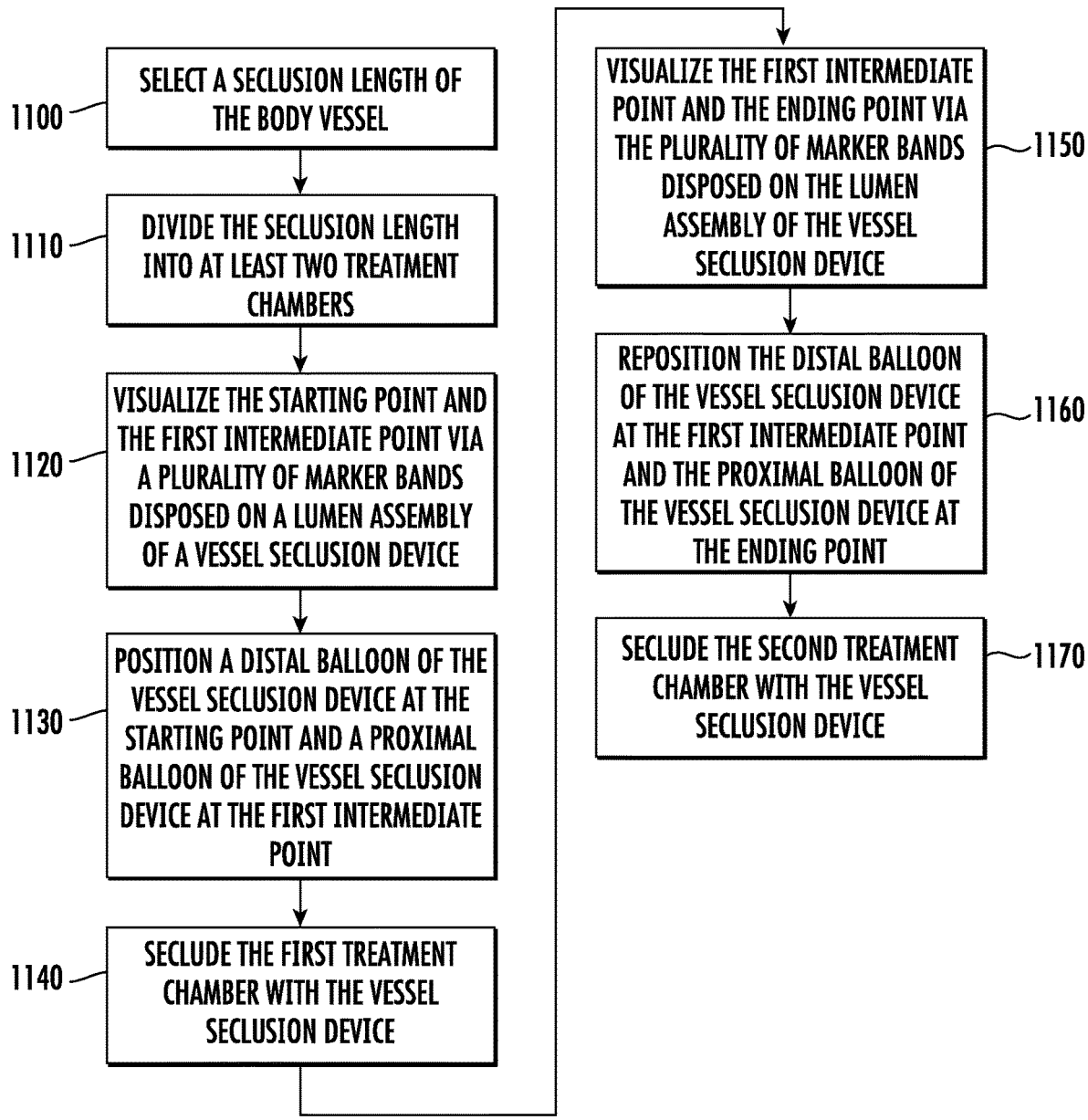
FIG. 11 illustrates a block diagram of a method of secluding a body vessel using the marking system according to an example embodiment.

Referring now to Block 1100 of FIG. 11, an example embodiment of the method of permanently secluding a body vessel includes selecting a seclusion length of the body vessel, the seclusion length having a starting point and an ending point. As discussed above, the seclusion length may depend on various factors. For example, the seclusion length may be based on the length of a body vessel to be treated (e.g., the body vessel seclusion device may be capable of treating a certain number of consecutive treatment chambers without removal based on the seclusion length).

Referring now to Block 1110 of FIG. 11, an example embodiment of the method of permanently secluding a body vessel includes dividing the seclusion length into at least two treatment chambers. In some embodiments, the at least two treatment chambers of the seclusion length include a first treatment chamber defined by the starting point and a first intermediate point and a second treatment chamber defined by the first intermediate point and the ending point. For example, as shown in FIG. 10A, the marker 1000 may be a starting point, the marker 1010 may be a first intermediate point, and the marker 1020 may be a ending point, such that moving the body seclusion device in relation to such markers may result in multiple treatment chambers being treated.

Referring now to Block 1120 of FIG. 11, an example embodiment of the method of permanently secluding a body vessel includes visualizing the starting point and the first intermediate point via a plurality of marker bands disposed on a lumen assembly of a vessel seclusion device. In various embodiments, the location of the marker bands at a given time may be compared to a reference point along the body vessel (e.g., the incision location into the body vessel or the like). For example, in an instance in which the seclusion device is within the body vessel, a given marker (e.g., the marker 1040 most proximal to the manifold 1050 shown in FIG. 10A) may be even with the incision point. In various embodiments, the distance between the incision point and the starting point of the body vessel may be determined based on the number of markers that are visible within the body vessel (e.g., visible via ultrasound). For example, a user may know the distance between markers and a set number of markers within the body vessel may indicate the distance from the incision point to the end of the lumen assembly 10, the distal balloon 30, and/or the proximal balloon 20.

Referring now to Block 1130 of FIG. 11, an example embodiment of the method of permanently secluding a body vessel includes positioning a distal balloon of the vessel seclusion device at the starting point and a proximal balloon of the vessel seclusion device at the first intermediate point. As stated in reference to Block 1120, the position of the proximal balloon 20 and the distal balloon 30 may be determined via the marking system. In an example embodiment, the starting point may be the point farthest from the incision point that the body vessel will be secluded. As discussed herein, the seclusion device may then be successively moved along the body vessel as each portion is secluded in order to permanently seclude the desired length of the body vessel.

Referring now to Block 1140 of FIG. 11, an example embodiment of the method of permanently secluding a body vessel includes secluding the first treatment chamber with the vessel seclusion device. As discussed above, a treatment chamber is a portion of the body vessel defined between the proximal balloon 20, the distal balloon 30, and the walls of body vessel. In some embodiments, the balloons 20, 30 may be independently inflated to contact the body vessel, such that the treatment area may be defined therein. In some embodiments, the body vessel may be secluded by first removing blood or a bodily fluid from the respective treatment chamber via an aspiration port lumen 15 having a plurality of aspiration ports 35 in fluid communication with the respective treatment chamber. In some embodiments, once the blood or a bodily fluid has been removed from the respective treatment chamber (e.g., the first treatment chamber), a chemical agent may be delivered to the respective treatment chamber via an injection port lumen 14 having a plurality of injection ports 25 in fluid communication with the respective treatment chamber. In some embodiments, the chemical agent may be kept in the treatment chamber for a predetermined amount of time (e.g., up to one minute). In some embodiments, the chemical agent may be removed from the respective treatment chamber via the aspiration port lumen 15 after the predetermined amount of time. In some embodiments, the proximal balloon 20 and the distal balloon may then be independently deflated in order to move the body seclusion device along the body vessel to define another treatment chamber (e.g., adjacent the prior treatment chamber) or for the body seclusion device to be removed from the body vessel if the seclusion is complete. In various embodiments, the ability to move and define successive adjacent treatment chamber may allow for the seclusion of a length of the body vessel that is longer than the length of the treatment chamber.

Referring now to Block 1150 of FIG. 11, an example embodiment of the method of permanently secluding a body vessel includes visualizing the first intermediate point and the ending point via the plurality of marker bands disposed on the lumen assembly of the vessel seclusion device. In various embodiments, the visualization may be completed via ultrasound. For example, the user of the seclusion device may use an ultrasound device to determine the number of markers (e.g., marker 1000-1040) that are within the body vessel. In some embodiments, the visualization may be based on the position of the lumen assembly in comparison to the incision point. For example, the positioning from a first treatment chamber to the second treatment chamber may be completed by removing a section of the lumen assembly from the body vessel in order to move from one treatment chamber to another treatment chamber (e.g., a user may be able to identify the position of the treatment chamber based on the number of markers that are outside of the body vessel).

Referring now to Block 1160 of FIG. 11, an example embodiment of the method of permanently secluding a body vessel includes repositioning the distal balloon of the vessel seclusion device at the first intermediate point and the proximal balloon of the vessel seclusion device at the ending point. As discussed above, the movement of the proximal balloon 20 and the distal balloon 30 along the body vessel may be less than the distance between the proximal balloon 20 and the distal balloon 30.

Referring now to Block 1170 of FIG. 11, an example embodiment of the method of permanently secluding a body vessel includes secluding the second treatment chamber with the vessel seclusion device. In various embodiments, the seclusion of the second treatment chamber is accomplished using the same as the seclusion process of the first treatment chamber discussed in reference to Block 1140 above. In various embodiments, the first treatment chamber and the second treatment chamber may be overlapping. In some embodiments, the first treatment chamber and the second treatment chamber may overlap by approximately 0.1 centimeters (cm) to 1.5 cm. In some embodiments, the first treatment chamber and the second treatment chamber may overlap by approximately 0.25 cm to 1 cm. In some embodiments, the first treatment chamber and the second treatment chamber may overlap by approximately 0.5 centimeters. In various embodiments, the overlapping of the treatment chambers may be based on the spacing between each marker (e.g., the overlap may be the difference between the distance between the balloons 20, 30 and the distance between the markers). In some embodiments, there may be little to no overlapping of treatment chambers, such that each treatment chamber starts approximately where the previous treatment chamber ended. In some embodiments, the steps discussed herein may be repeated, such that there are more than two treatment chambers (e.g., a third treatment chamber, a fourth treatment chamber, etc.), depending on the desired length of the body vessel to be treated.

Figure 12:
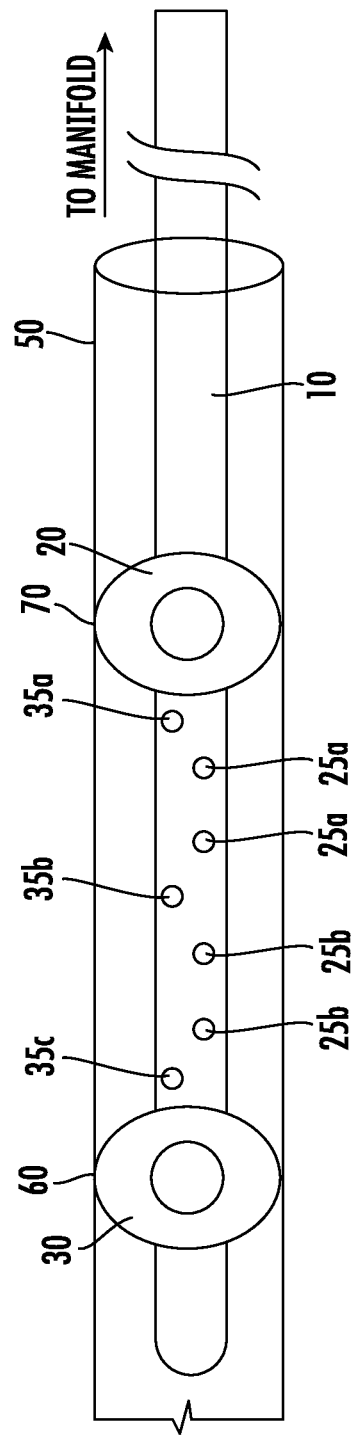
FIG. 12 illustrates a partial view of a device for secluding a body vessel in a deployed form according to an example embodiment.

FIG. 12 illustrates an additional lumen assembly in accordance with an example embodiment. In some embodiments, the lumen assembly 10 may have a plurality of aspiration ports 35 along the aspiration port lumen 14. In some embodiments, the lumen assembly 10 may have a plurality of injection ports 25 along the injection port lumen 15. In some embodiments, the plurality of injection ports 25 and/or the plurality of aspiration ports 35 may be distributed between the proximal balloon 20 and the distal balloon 30. In some embodiments, the aspiration port lumen 14 may include three aspiration ports. For example, the aspiration port lumen 14 may include a proximal aspiration port 35*a*, an intermediate aspiration port 35*b*, and a distal aspiration port 35*c*. In some embodiments, the injection port lumen 15 may include four injection ports. In some embodiments, the injection port lumen 15 may include a first set of two injection ports 25*a* and a second set of two injection ports 25*b*. In some embodiments, the first set of two injection ports 25*a* is disposed between the proximal aspiration port 35*a* and the intermediate aspiration port 35*b* in the treatment chamber. In some embodiments, the second set of two injection ports 25*b* is disposed between the intermediate aspiration port 35*b* and the distal aspiration port 35*c* in the treatment chamber. While the plurality of injection ports 25 and the plurality of aspiration ports 35 are discussed in reference to the example configuration shown in FIG. 12, other configurations of the plurality of injection ports 25 and the plurality of aspiration ports 35 may be used.

Exemplary Embodiments

Certain exemplary embodiments provide a device for secluding a body vessel. For instance, this device provides a less invasive, less damaging means for secluding body vessels having a reduced recovery time and that is less likely to require multiple applications. In one aspect, the device for secluding a body vessel includes a distal balloon, a proximal balloon, an aspiration port positioned adjacent to the distal balloon, an injection port positioned adjacent to the proximal balloon, and a lumen assembly. According to certain embodiments, the lumen assembly comprises a central lumen, a distal balloon lumen operably coupled to the distal balloon, a proximal balloon lumen operably coupled to the proximal balloon, an aspiration port lumen operably coupled to the aspiration port, and an injection port lumen operably coupled to the injection port. In some embodiments, the distal balloon and the proximal balloon define a treatment chamber therebetween, and the aspiration port and the injection port are positioned within the treatment chamber on the lumen assembly. In certain embodiments, the treatment chamber comprises a length from about 3 cm to about 15 cm. In further embodiments, the central lumen is configured to introduce a guide wire into the body vessel.

In accordance with certain embodiments, each of the aspiration port and the injection port comprise a port orifice and a one-way valve at the port orifice. In some embodiments, the aspiration port and the aspiration port lumen are configured to remove at least one of blood, bodily fluid, a chemical agent, or any combination thereof from the treatment chamber. In further embodiments, the injection port and the injection port lumen are configured to deliver a chemical agent to the treatment chamber.

According to certain embodiments, each of the distal balloon and the proximal balloon are spherical. In some embodiments, the distal balloon comprises an inflated distal balloon diameter, the proximal balloon comprises an inflated proximal balloon diameter, and each of the inflated distal balloon diameter and the inflated proximal balloon diameter is from about 5 mm to about 20 mm.

In another aspect, certain embodiments provide a method for secluding a body vessel. According to certain embodiments, the method includes removing blood from a treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port. In such embodiments, the aspiration port is operably coupled to an aspiration port lumen of a vessel seclusion device, and the injection port is operably coupled to an injection port lumen of the vessel seclusion device. In some embodiments, the body vessel comprises at least one of a varicose vein, a portal vein, a perforator vein, a superficial vein, a peripheral vein, an arteriovenous malformation, or any combination thereof.

In accordance with certain embodiments, maintaining the chemical agent in the treatment chamber for the predetermined period of time comprises maintaining the chemical agent in the treatment chamber from about 1 second to about 60 seconds. In some embodiments, the chemical agent comprises a sclerosing agent.

In accordance with certain embodiments, the method further comprises inserting a guide wire into the body vessel via a central lumen of the vessel seclusion device. In such embodiments, the method further comprises inserting at least a portion of the vessel seclusion device into the body vessel via the guide wire. In further embodiments, the method further comprises positioning the vessel seclusion device with the body vessel via ultrasound. In some embodiments, the method further comprises inflating a distal balloon and a proximal balloon of the vessel seclusion device within the body vessel to define the treatment chamber. In such embodiments, inflating the distal balloon and the proximal balloon comprises separately inserting a fluid into the distal balloon via a distal balloon lumen and inserting the fluid into the proximal balloon via a proximal balloon lumen.

In yet another aspect, certain embodiments provide a method for secluding a body vessel. According to certain embodiments, the method includes selecting a seclusion length of the body vessel such that the seclusion length has a starting point and an ending point, dividing the seclusion length into at least two treatment chambers, secluding the first treatment chamber with a vessel seclusion device, moving the vessel seclusion device to the second treatment chamber, and secluding the second treatment chamber. In such embodiments, the first treatment chamber is defined by the starting point and a first intermediate point, and the second treatment chamber is defined by the first intermediate point and the ending point. In some embodiments, secluding each of the first treatment chamber and the second treatment chamber comprises removing blood from the treatment chamber in the body vessel via an aspiration port, delivering a chemical agent to the treatment chamber via an injection port, maintaining the chemical agent in the treatment chamber for a predetermined period of time to seclude the body vessel within the treatment chamber, and removing the chemical agent from the treatment chamber via the aspiration port. In such embodiments, the aspiration port is operably coupled to an aspiration port lumen of a vessel seclusion device, and the injection port is operably coupled to an injection port lumen of the vessel seclusion device. According to certain embodiments, moving the vessel seclusion device comprises positioning the vessel seclusion device within the body vessel via ultrasound.

In accordance with certain embodiments, the seclusion length comprises at least three treatment chambers. In such embodiments, the first treatment chamber is defined by the starting point and the first intermediate point, the second treatment chamber is defined by the first intermediate point and a second intermediate point, and a third treatment chamber is defined by the second intermediate point and the ending point.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

What is claimed is:

1. A lumen assembly of a device for permanently closing off a vein, the lumen assembly comprising:
    an aspiration port lumen having a cross-section defined by an aspiration port lumen circumference, the aspiration port lumen defining a plurality of aspiration ports, the aspiration port lumen and the plurality of aspiration ports being configured to remove at least one of blood, a bodily fluid, a chemical agent for permanently closing off the vein, or any combination thereof from a treatment chamber in the vein;
    an injection port lumen having a cross-section defined by an injection port lumen circumference, the injection port lumen defining a plurality of injection ports, the injection port lumen and the plurality of injection ports being configured to deliver the chemical agent for permanently closing off the vein to the treatment chamber;
    a proximal balloon lumen having a cross-section defined by a proximal balloon lumen circumference, the proximal balloon lumen being configured to adjust an inflation level of a proximal balloon that defines a proximal end of the treatment chamber; and
    a distal balloon lumen having a cross-section defined by a distal balloon lumen circumference, the distal balloon lumen being configured to adjust an inflation level of a distal balloon that defines a distal end of the treatment chamber;
    a first transverse axis defined along a cross-section of the lumen assembly; and
    a second transverse axis defined along the cross-section of the lumen assembly, wherein the second transverse axis is perpendicular to the first transverse axis,
    wherein each of the aspiration port lumen circumference, the injection port lumen circumference, the distal balloon lumen circumference, and the proximal balloon lumen circumference is generally circular;
    wherein the aspiration port lumen comprises an aspiration port lumen diameter, the aspiration port lumen diameter extending linearly from a first point on the aspiration port lumen circumference to a second point on the aspiration port lumen circumference and intersecting a cross sectional center- point of the aspiration port lumen;
    wherein the injection port lumen comprises an injection port lumen diameter, the injection port lumen diameter extending linearly from a first point on the injection port lumen circumference to a second point on the injection port lumen circumference and intersecting a cross sectional center-point of the injection port lumen;

wherein the aspiration port lumen diameter, the injection port lumen diameter, and the first transverse axis are colinear;

wherein the proximal balloon lumen comprises a proximal balloon lumen diameter, the proximal balloon lumen diameter extending linearly from a first point on the proximal balloon lumen circumference to a second point on the proximal balloon lumen circumference and intersecting a cross sectional center-point of the proximal balloon lumen;

wherein the distal balloon lumen comprises a distal balloon lumen diameter, the distal balloon lumen diameter extending linearly from a first point on the distal balloon lumen circumference to a second point on the distal balloon lumen circumference and intersecting a cross sectional center-point of the distal balloon lumen;

wherein the proximal balloon lumen diameter, the distal balloon lumen diameter, and the second transverse axis are colinear;

wherein each of the aspiration port lumen diameter and the injection port lumen diameter are larger than each of the proximal balloon lumen diameter and the distal balloon lumen diameter; and wherein the lumen assembly does not include a dedicated guide wire lumen.

2. The lumen assembly of claim 1, wherein the first transverse axis is vertical, and the second transverse axis is horizontal.

3. The lumen assembly of claim 1, wherein the plurality of aspiration ports are evenly spaced on the aspiration port lumen.

4. The lumen assembly of claim 1, wherein the plurality of aspiration ports comprises three aspiration ports, and the plurality of injection ports comprises four injection ports.

5. The lumen assembly of claim 4, wherein the three aspiration ports comprise a proximal aspiration port, an intermediate aspiration port, and a distal aspiration port, the four injection ports comprise a first set of two injection ports and a second set of two injection ports, the first set of two injection ports is disposed between the proximal aspiration port and the intermediate aspiration port in the treatment chamber, and the second set of two injection ports is disposed between the intermediate aspiration port and the distal aspiration port in the treatment chamber.

6. The lumen assembly of claim 1, wherein the lumen assembly has the same length as the device for permanently closing off the vein.

7. The lumen assembly of claim 1, wherein the proximal balloon lumen and the distal balloon lumen are configured to independently inflate the proximal balloon and the distal balloon respectively.

8. The lumen assembly of claim 1, wherein the lumen assembly defines a perimeter, wherein a sum of the aspiration port lumen diameter and the injection port lumen diameter comprises at least half a length of the first transverse axis defined between a first point on the perimeter and a second point on the perimeter.

9. The lumen assembly of claim 1 wherein the first transverse axis and the second transverse axis intersect at a cross-sectional center-point of the lumen assembly.

10. The lumen assembly of claim 9, wherein the cross-sectional center point of the lumen assembly does not coincide with a lumen of the lumen assembly.

11. A method of permanently closing off a vein with a device having a lumen assembly for permanently closing off the vein, the method comprising:

guiding the device into position in the vein via the lumen assembly, wherein the lumen assembly comprises:

an aspiration port lumen having a cross-section defined by an aspiration port lumen circumference, the aspiration port lumen defining a plurality of aspiration ports, the aspiration port lumen and the plurality of aspiration ports being configured to remove at least one of blood, a bodily fluid, a chemical agent for permanently closing off the vein, or any combination thereof from a treatment chamber in the vein;

an injection port lumen having a cross-section defined by an injection port lumen circumference, the injection port lumen defining a plurality of injection ports, the injection port lumen and the plurality of injection ports being configured to deliver the chemical agent for permanently closing off the vein to the treatment chamber;

a proximal balloon lumen having a cross-section defined by a proximal balloon lumen circumference, the proximal balloon lumen being configured to adjust an inflation level of a proximal balloon that defines a proximal end of the treatment chamber; and a distal balloon lumen having a cross-section defined by a distal balloon lumen circumference, the distal balloon lumen being configured to adjust an inflation level of a distal balloon that defines a distal end of the treatment chamber;

a first transverse axis defined along a cross-section of the lumen assembly; and a second transverse axis defined along the cross-section of the lumen assembly, wherein the second transverse axis is perpendicular to the first transverse axis, adjusting the inflation level of the distal balloon via the distal balloon lumen to define the distal end of a the treatment chamber;

adjusting the inflation level of the proximal balloon via the proximal balloon lumen to define the proximal end of the treatment chamber;

removing blood from the treatment chamber in the vein via the aspiration port lumen having the plurality of aspiration ports in fluid communication with the treatment chamber;

delivering a the chemical agent to the treatment chamber via the injection port lumen having the plurality of injection ports in fluid communication with the treatment chamber;

maintaining the chemical agent in the treatment chamber for a predetermined period of time such that the chemical agent causes the vein to collapse around the inflated distal balloon and proximal balloon such that the inflated distal balloon and proximal balloon support the vein;

removing the chemical agent from the treatment chamber via the aspiration port lumen;

deflating the distal balloon via the distal balloon lumen;

deflating the proximal balloon via the proximal balloon lumen; and removing the device from the treatment chamber, wherein the treatment chamber permanently closes around the device as the device is removed, wherein each of the aspiration port lumen circumference, the injection port lumen circumference, the distal balloon lumen circumference, and the proximal balloon lumen circumference is generally circular;

wherein the aspiration port lumen comprises an aspiration port lumen diameter, the aspiration port lumen diameter extending linearly from a first point on the aspiration port lumen circumference to a second point on the aspiration port lumen circumference and intersecting a cross sectional center- point of the aspiration port lumen;

wherein the injection port lumen comprises an injection port lumen diameter, the injection port lumen diameter extending linearly from a first point on the injection port lumen circumference to a second point on the injection port lumen circumference and intersecting a cross sectional center-point of the injection port lumen;

wherein the aspiration port lumen diameter, the injection port lumen diameter, and the first transverse axis are colinear;

wherein the proximal balloon lumen comprises a proximal balloon lumen diameter, the proximal balloon lumen diameter extending linearly from a first point on the proximal balloon lumen circumference to a second point on the proximal balloon lumen circumference and intersecting a cross sectional center-point of the proximal balloon lumen;

wherein the distal balloon lumen comprises a distal balloon lumen diameter, the distal balloon lumen diameter extending linearly from a first point on the distal balloon lumen circumference to a second point on the distal balloon lumen circumference and intersecting a cross sectional center-point of the distal balloon lumen;

wherein the proximal balloon lumen diameter, the distal balloon lumen diameter, and the second transverse axis are colinear;

wherein each of the aspiration port lumen diameter and the injection port lumen diameter are larger than each of the proximal balloon lumen diameter and the distal balloon lumen diameter; and wherein the lumen assembly does not include a dedicated guide wire lumen.

12. The method of claim 11, wherein the proximal balloon lumen and the distal balloon lumen are configured to independently inflate the proximal balloon and the distal balloon respectively.

13. The method of claim 11, wherein the first transverse axis is vertical, and the second transverse axis is horizontal.

14. The method of claim 11, wherein the plurality of aspiration ports are evenly spaced on the aspiration port lumen.

15. The method of claim 11, wherein the aspiration port lumen comprises three aspiration ports, and the injection port lumen comprises four injection ports.

16. The method of claim 15, wherein the three aspiration ports comprise a proximal aspiration port, an intermediate aspiration port, and a distal aspiration port, the four injection ports comprise a first set of two injection ports and a second set of two injection ports, the first set of two injection ports is disposed between the proximal aspiration port and the intermediate aspiration port in the treatment chamber, and the second set of two injection ports is disposed between the intermediate aspiration port and the distal aspiration port in the treatment chamber.

17. The method of claim 11, wherein the lumen assembly has the same length as the device.

* * * * *